(12) United States Patent
Santra et al.

(10) Patent No.: US 10,070,651 B2
(45) Date of Patent: Sep. 11, 2018

(54) SYNTHESIS AND CHARACTERIZATION OF ANTIMICROBIAL NON-COLOR FORMING SILVER-SILICA NANOCOMPOSITE

(71) Applicant: UNIVERSITY OF CENTRAL FLORIDA RESEARCH FOUNDATION, INC., Orlando, FL (US)

(72) Inventors: Swadeshmukul Santra, Oviedo, FL (US); Joshua J. Bazata, Winter Springs, FL (US)

(73) Assignee: UNIVERSITY OF CENTRAL FLORIDA RESEARCH FOUNDATION, INC., Orlando, FL (US)

(*) Notice: Subject to any disclaimer, the term of this patent is extended or adjusted under 35 U.S.C. 154(b) by 0 days.

(21) Appl. No.: 15/292,523

(22) Filed: Oct. 13, 2016

(65) Prior Publication Data

US 2017/0099842 A1    Apr. 13, 2017

Related U.S. Application Data

(60) Provisional application No. 62/240,849, filed on Oct. 13, 2015.

(51) Int. Cl.
| | | |
|---|---|---|
| *C09C 1/30* | (2006.01) | |
| *B82Y 30/00* | (2011.01) | |
| *B22F 9/24* | (2006.01) | |
| *B22F 1/02* | (2006.01) | |
| *B22F 1/00* | (2006.01) | |

(Continued)

(52) U.S. Cl.
CPC ............. *A01N 59/16* (2013.01); *A01N 25/28* (2013.01); *B22F 1/0018* (2013.01); *B22F 1/0044* (2013.01); *B22F 1/02* (2013.01); *B22F 9/24* (2013.01); *B82Y 30/00* (2013.01);
(Continued)

(58) Field of Classification Search
None
See application file for complete search history.

(56) References Cited

U.S. PATENT DOCUMENTS 9,247,734 B2   2/2016   Sabin
9,717,251 B2   8/2017   Sabin
(Continued)

OTHER PUBLICATIONS

Xu et al., "Fabrication of antibacterial monodispersed Ag—SiO2 core-shell nanoparticles with high concentration", Materials Letters 63 (2009) 31-33.*

(Continued)

*Primary Examiner* — Ernst V Arnold
*Assistant Examiner* — Kyung Sook Chang
(74) *Attorney, Agent, or Firm* — Bond Schoeneck & King, PLLC; George McGuire

(57) ABSTRACT

The present invention relates to, inter alia, a composition, a nanocomposite material, and a method for preparing the nanocomposite material. The nanocomposite material includes: a dielectric-silver nanocomposite material, the dielectric-silver nanocomposite material including a silver nanoparticle having a silver ion, and a dielectric material encapsulating the silver nanoparticle, where the silver ion chelates with a matrix of the dielectric material, and a surface plasmon band absorption of the dielectric-silver nanocomposite material lies outside a range of a visible region.

21 Claims, 15 Drawing Sheets

(51) Int. Cl.
*A01N 25/28* (2006.01)
*A01N 59/16* (2006.01)
*C09D 5/14* (2006.01)
*C01B 33/18* (2006.01)

(52) U.S. Cl.
CPC ............ *C01B 33/18* (2013.01); *C09C 1/3054* (2013.01); *C09D 5/14* (2013.01)

(56) References Cited

U.S. PATENT DOCUMENTS 9,718,739 B2    8/2017  Sabin
2013/0108678 A1*  5/2013  Santra .................... A01N 59/16
                                                  424/409

OTHER PUBLICATIONS

Jaiswal et al., "Enhancement of the antibacterial properties of silver nanoparticles using beta-cyclodextrin as a capping agent", International Journal of Antimicrobial Agents 36 (2010) 280-283.*
EL Badawy et al., "Key Factors Controlling the Transport of Silver Nanoparticles in Porous Media", Environmental science & technology, American Chemical Society, 2013, pp. 4039-4045.*
Egger et al., "Antimicrobial Properties of a Novel Silver-Silica Nanocomposite Material", Applied and Environmental Microbiology, May 2009, pp. 2973-2976.*
Morita, Makoto, et al., Silver Nitrate Impregnation of Preparative Silica Gel Columns for Liquid Chromatography, Anal. Chem. 1983, 55, 412-414.
Sigma Aldrich Product Catalog, Silver Nitrate on Silica gel extent of labeling, http://www.sigmaaldrich.com/catalog/product/aldrich/248762?lang=en&region=US, as of Oct. 13, 2016, pp. 1-4.
Hebert, John Environmental Protection Agency Letter to HeiQ Materials AG dated Dec. 17, 2013; 4 pages.
Young, Mikaeel, et al.; Multimodal generally Recognized as Safe ZnO/Nanocopper Composite: A Novel Antimicrobial Material for the Management of Citrus Phytopathogens; Journal of Agriculture and Food Chemistry; Publication Date (Web) Aug. 23, 2017; Copyright 2017 American Chemical Society; 7 pages.

* cited by examiner

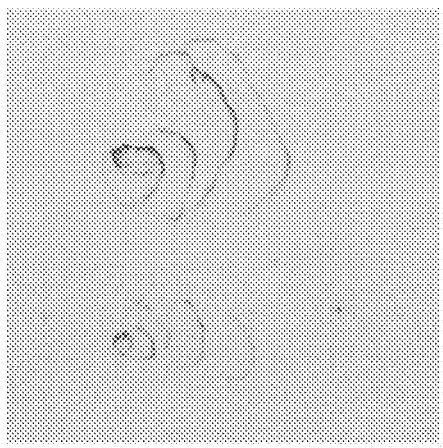
FIG. 9A
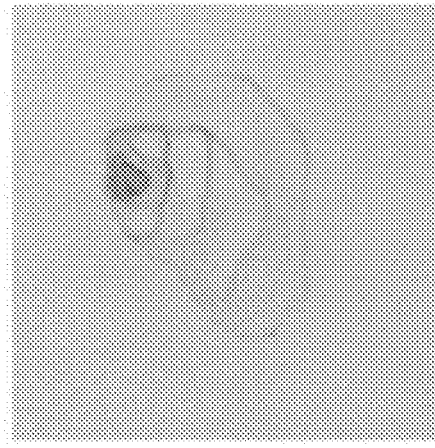
FIG. 9B
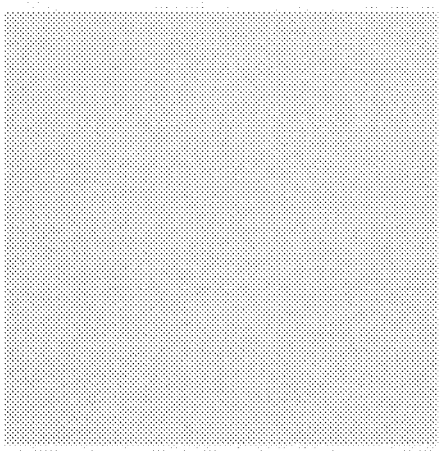
FIG. 9C
FIG. 9D

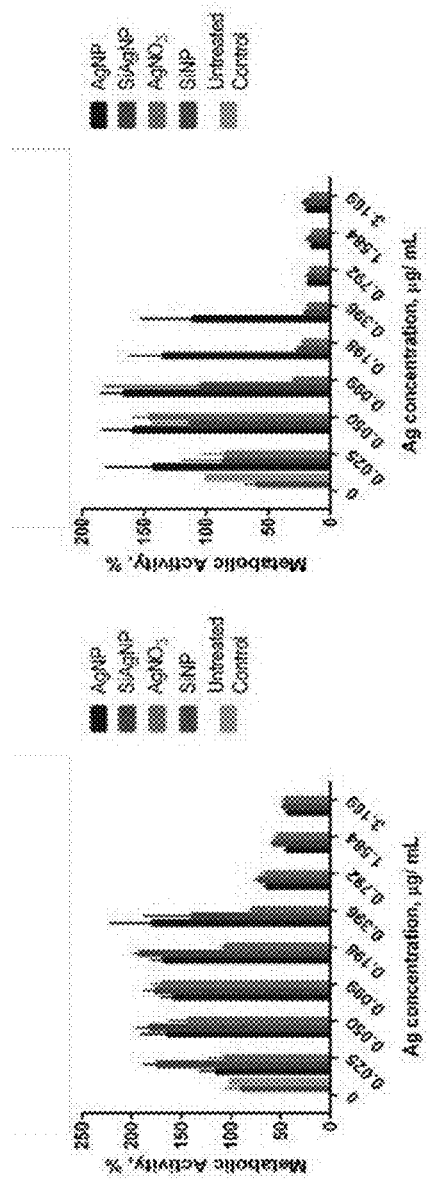
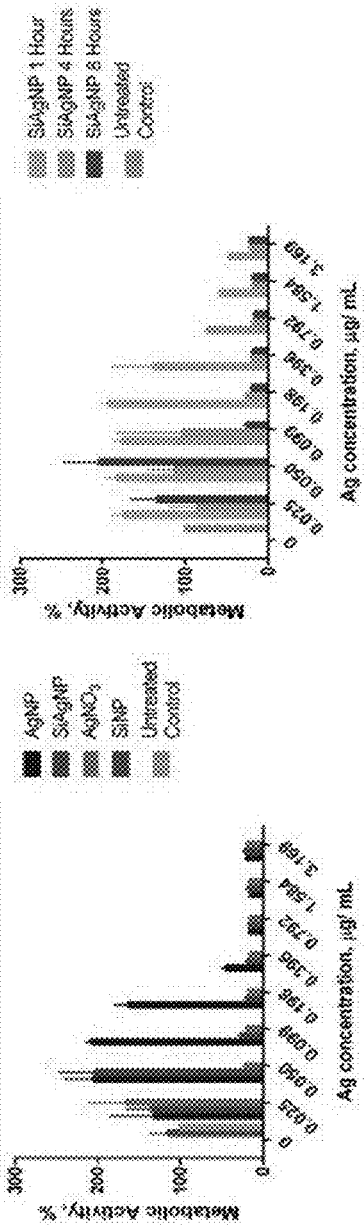
FIG. 10A
FIG. 10B
FIG. 10C
FIG. 10D

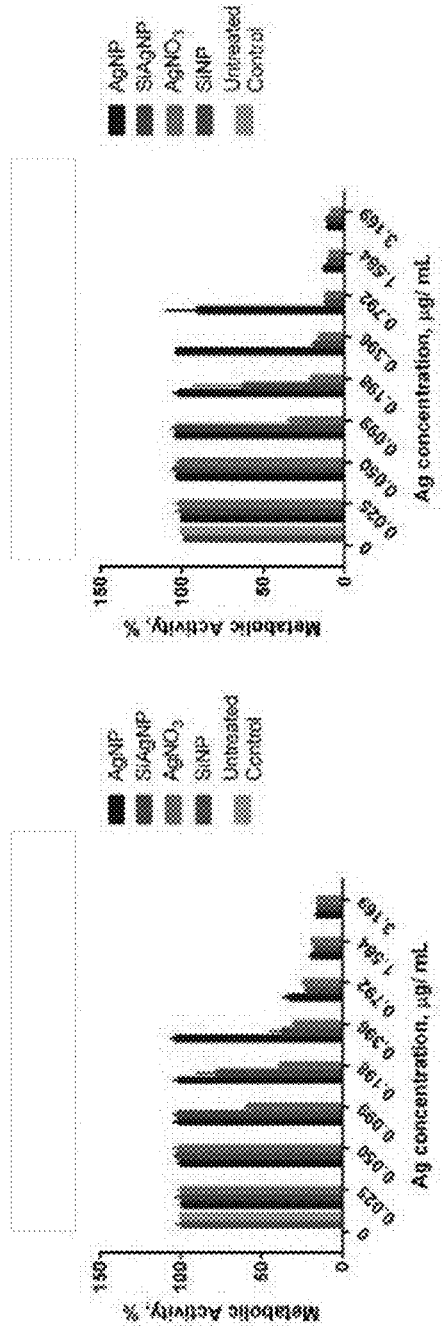
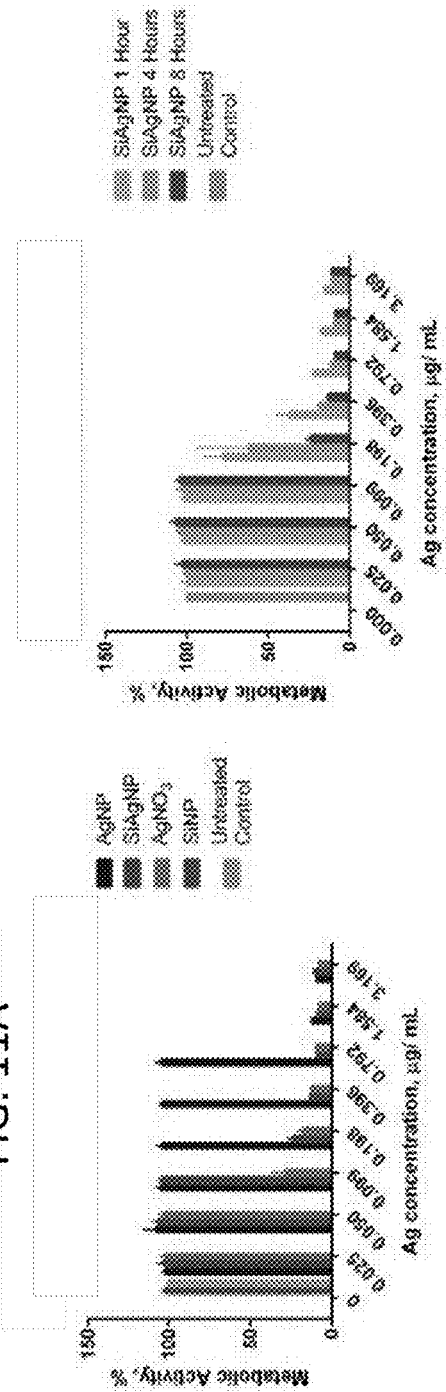
FIG. 11A
FIG. 11B
FIG. 11C
FIG. 11D

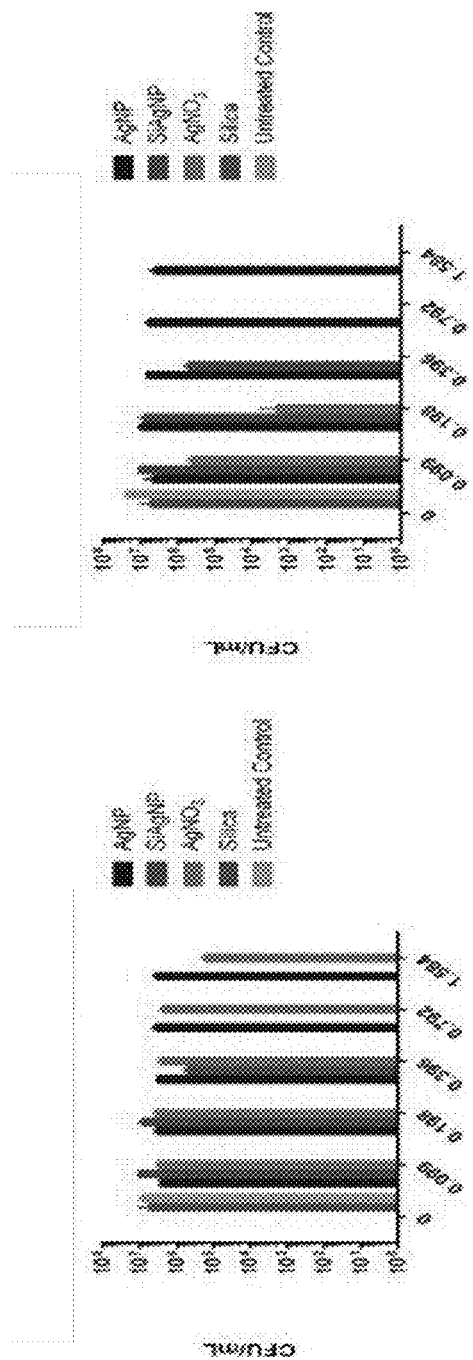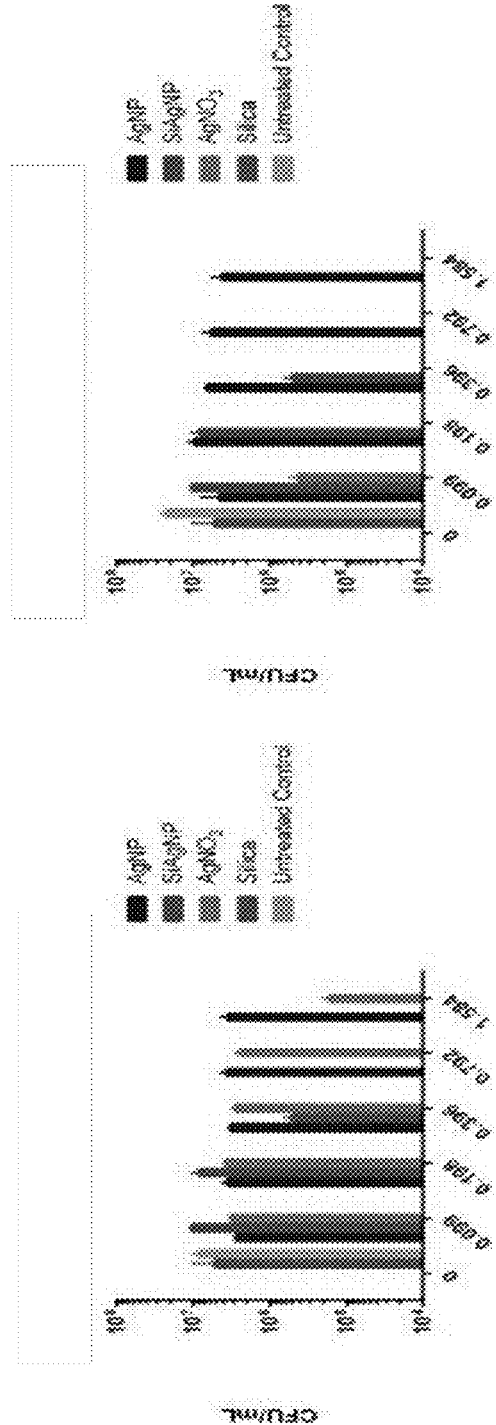

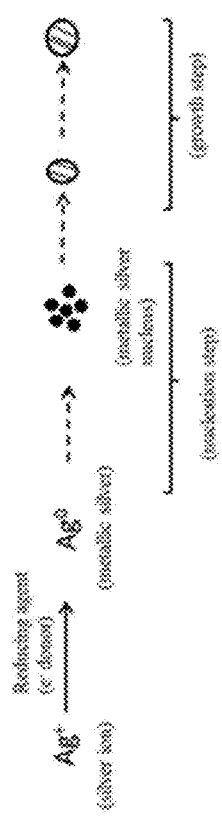

SYNTHESIS AND CHARACTERIZATION OF ANTIMICROBIAL NON-COLOR FORMING SILVER-SILICA NANOCOMPOSITE

STATEMENT OF GOVERNMENT INTEREST

The embodiments as disclosed herein and the invention as claimed herein were funded by the United States National Science Foundation under Grant Number 0506560. The United States Government has rights in the invention as claimed herein.

CROSS-REFERENCE TO RELATED APPLICATION

This application is related to, and derives from, U.S. Provisional Patent Application Ser. No. 62/240,849, filed 13 Oct. 2015 and titled "Synthesis And Characterization of Antimicrobial Non-Color Forming Silver-Silica Nanocomposite."

BACKGROUND

Silver, as an antimicrobial agent, continues to be a growing area of interest across many industries such as, medicinal, pharmaceutical and aeronautical, although silver has traditionally been valued for its ductility and luster. For instance, silver nitrate has been used for treating eye diseases in infants, while silver sulfadiazine has been used for topical administration in the healthcare industry. As understood, these compounds take advantage of enhanced potency of the silver ($Ag^+$) ion against microbes, while leaving eukaryotic cells unharmed when applied topically at microbicidal concentrations. For instance, silver ($Ag^+$) ion binds to sulfur and/or phosphorus atoms within a cell, disrupting protein and DNA structures, which, for instance, leads to inhibition of essential cellular processes, membrane disruption, and DNA damage. This, for instance, eventually results in the death of the cell. In another example, silver also induces decoupling of the respiratory chain, leading to cell death.

Additionally, owing to their antimicrobial characteristics, silver or silver-containing products are often utilized as antimicrobial coatings over surfaces, such as, toilet handles, pens, door knobs, and aircraft surfaces, to minimize fomite-mediated transmission of microbes. Disadvantageously, silver coatings cause discolorations, (for example, unpleasant dark brown to grey color) of such surfaces, due to aggregation of silver particles which, for instance, leads to a strong plasmon signal. As understood, metallic silver exhibits high plasmonic efficiency, due to collective oscillation of valence electrons of silver, when an incident photon matches the resonant frequencies of the valence electrons, leading to emission of that energy as a photon which, for instance, can be confirmed by a strong silver peak in its corresponding UV-Visible spectrum.

Accordingly, there exists a continuing need for developing novel silver-containing products that remain colorless (for instance, visibly indistinguishable from an untreated surface, upon coating), without compromising its antimicrobial efficacy.

SUMMARY

The present invention is directed to, inter alia, a composition having a dielectric-silver nanocomposite material having antimicrobial characteristics, a nanocomposite material, and a method for preparing a nanocomposite material of the same. The dielectric-silver nanocomposite material includes a silver nanoparticle that is co-loaded with ionic silver, where the silver from each of the silver nanoparticle and the ionic silver chelates with a dielectric material, such as, silica. A surface plasmon band absorption of the dielectric-silver nanocomposite material lies outside a range of a visible region, resulting in its transparency. Further, a sustained release of each of the silver nanoparticle and the ionic silver from the dielectric-silver nanocomposite particle promotes its antimicrobial characteristics, without affecting the transparency of the dielectric-silver nanocomposite material.

In one aspect of the present application, a composition including: a dielectric-silver nanocomposite material, the dielectric-silver nanocomposite material including a silver nanoparticle that is co-loaded with an ionic silver, and a dielectric material encapsulating each of the silver nanoparticle and the ionic silver, wherein silver from each of the silver nanoparticle and the ionic silver chelates with a matrix of the dielectric material, and a surface plasmon band absorption of the dielectric-silver nanocomposite material lies outside a range of a visible region.

In another aspect of the present application, a nanocomposite material including: a silver nanoparticle that is co-loaded with an ionic silver, and a dielectric material encapsulating each of the silver nanoparticle and the ionic silver to form a dielectric-silver nanocomposite material, wherein silver from each of the silver nanoparticle and the ionic silver chelates with a matrix of the dielectric material, and a surface plasmon band absorption of the dielectric-silver nanocomposite material lies outside a range of a visible region. In yet another aspect of the present application, a method for preparing a nanocomposite material, the method including: mixing an aqueous solution of a silver-precursor with an aqueous solution of a capping-agent precursor in presence of a reducing agent at 0° C. to form a mixture I, the mixture I comprising a capping-agent-coated silver nanoparticle and an ionic silver; and mixing an aqueous solution of the mixture I with a dielectric-material precursor in an organic solvent to form a dielectric-silver nanocomposite material, the dielectric-silver nanocomposite material including the capping-agent-coated silver nanoparticle that is co-loaded with the ionic silver, and a dielectric material encapsulating each of the capping-agent-coated silver nanoparticle and the ionic silver, wherein silver from each of the capping-agent-coated silver nanoparticle and the ionic silver chelates with a matrix of a dielectric material, and a surface plasmon band absorption of the dielectric-silver nanocomposite material lies outside a range of a visible region.

Other compositions, methods, features, and advantages will be, or become, apparent to one with skill in the art upon examination of the following drawings and detailed description.

BRIEF DESCRIPTION OF THE DRAWINGS

Many aspects of this disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIGS. 9A-9H depict comparative examples of color passivation testing of the silica-silver nanocomposite material, that is subjected to thermal and UV treatments relative to those of the controls, in accordance with one or more aspects of the present invention.

FIGS. 10A-10D illustrate a graphical representation of one embodiment of antimicrobial efficacy of the silica-silver nanocomposite material relative to that of the silver nanoparticle lacking the silica matrix and the silica nanoparticle, respectively, for a Gram Positive cocci, (for example, *S. aureus*), in accordance with one or more aspects of the present invention.

FIGS. 11A-11D illustrate a graphical representation of one embodiment of antimicrobial efficacy of the silica-silver nanocomposite material relative to that of the silver nanoparticle lacking the silica matrix and the silica nanoparticle, respectively, for a Gram Negative rod, (for example, *E. coli*), in accordance with one or more aspects of the present invention.

FIGS. 13A-13D show a graphical representation of one embodiment of colony forming unit (CFU) study of the silica-silver nanocomposite material with respect to the Gram Negative rod (for instance, *E. coli*), in accordance with one or more aspects of the present invention.

FIG. 14 illustrates a schematic representation of forming a silver nanoparticle, prior to being coated with a dielectric material, in accordance with one or more aspects of the present invention.

DETAILED DESCRIPTION

Figure 1:
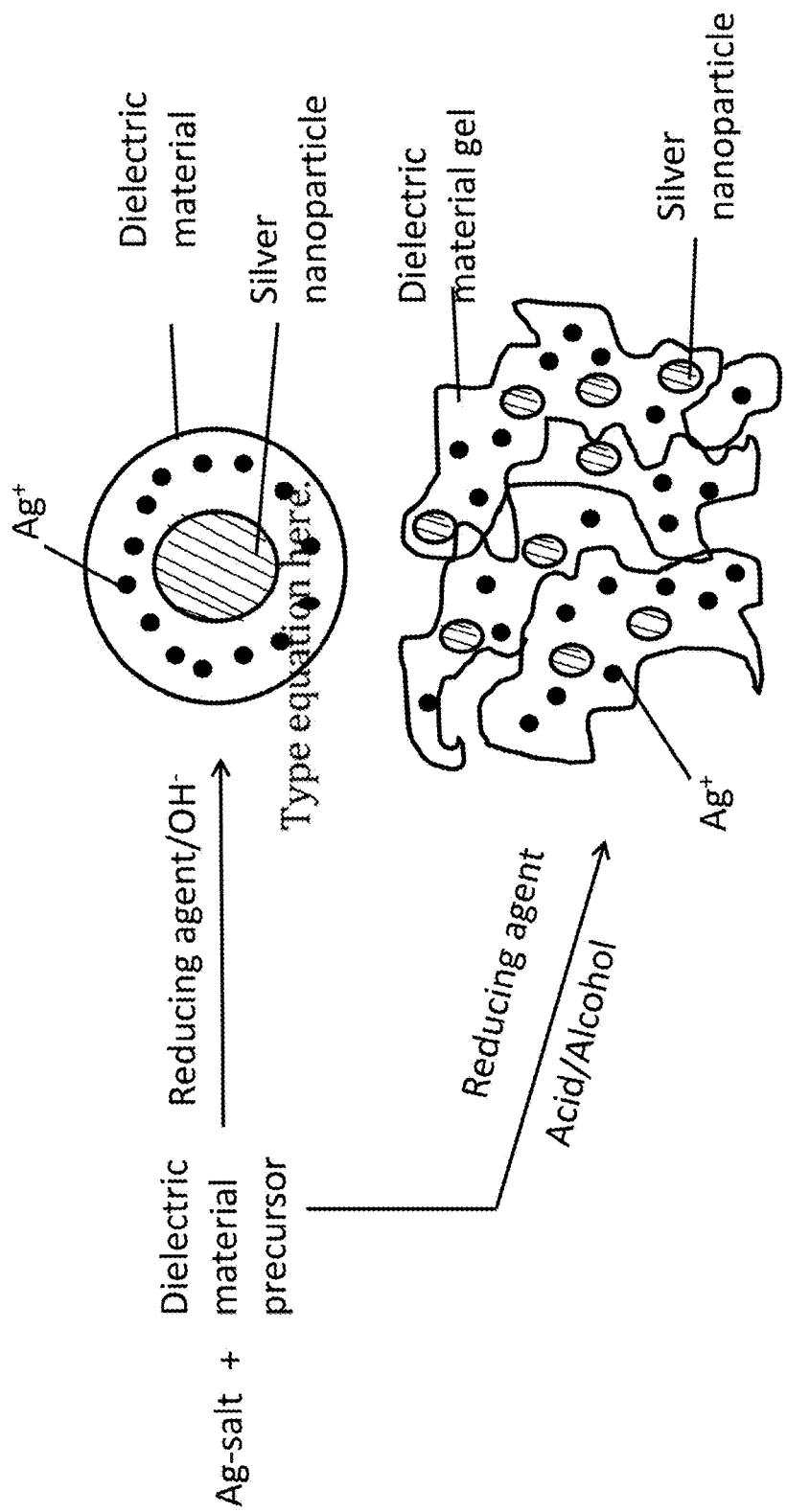
FIG. 1 illustrates a schematic representation of preparing a dielectric-silver nanocomposite material which includes, for instance, a dielectric-silver nanocomposite particle, and a dielectric-silver nanocomposite gel, in accordance with one or more aspects of the present invention.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features that may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, polymer chemistry, biology, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is in atmospheres. Standard temperature and pressure are defined as 25° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Definitions (Which Are Not Necessarily Limited to the Present Disclosure):

The term "antimicrobial characteristic" refers to the ability to kill and/or inhibit the growth of microorganisms. A substance having an antimicrobial characteristic may be harmful to microorganisms (e.g., bacteria, fungi, protozoans, algae, and the like). A substance having an antimicrobial characteristic can kill the microorganism and/or prevent or substantially prevent or inhibit the growth or reproduction of the microorganism.

The term "antibacterial characteristic" refers to the ability to kill and/or inhibit the growth of bacteria. A substance having an antibacterial characteristic may be harmful to bacteria. A substance having an antibacterial characteristic can kill the bacteria and/or prevent or substantially prevent or inhibit the replication or reproduction of the bacteria.

The terms "bacteria" or "bacterium" include, but are not limited to, Gram positive and Gram negative bacteria. Bacteria can include, but are not limited to, *Abiotrophia, Achromobacter, Acidaminococcus, Acidovorax, Acinetobacter, Actinobacillus, Actinobaculum, Actinomadura, Actinomyces, Aerococcus, Aeromonas, Afipia, Agrobacterium, Alcaligenes, Alloiococcus, Alteromonas, Amycolata, Amycolatopsis, Anaerobospirillum, Anabaena affinis* and other cyanobacteria (including the *Anabaena, Anabaenopsis, Aphanizomenon, Camesiphon, Cylindrospermopsis, Gloeobacter Hapalosiphon, Lyngbya, Microcystis, Nodularia, Nostoc, Phormidium, Planktothrix, Pseudoanabaena, Schizothrix, Spirulina, Trichodesmium,* and *Umezakia* genera) *Anaerorhabdus, Arachnia, Arcanobacterium, Arcobacter, Arthrobacter, Atopobium, Aureobacterium, Bacteroides, Balneatrix, Bartonella, Bergeyella, Bifidobacterium, Bilophila Branhamella, Borrelia, Bordetella, Brachyspira, Brevibacillus, Brevibacterium, Brevundimonas, Brucella, Burkholderia, Buttiauxella, Butyrivibrio, Calymmatobacterium, Campylobacter, Capnocytophaga, Cardiobacterium, Catonella, Cedecea, Cellulomonas, Centipeda, Chlamydia, Chlamydophila, Chromobacterium, Chyseobacterium, Chryseomonas, Citrobacter, Clostridium, Collinsella, Comamonas, Corynebacterium, Coxiella, Cryptobacterium, Delftia, Dermabacter, Dermatophilus, Desulfomonas, Desulfovibrio, Dialister, Dichelobacter, Dolosicoccus, Dolosigranulum, Edwardsiella, Eggerthella, Ehrlichia, Eikenella, Empedobacter, Enterobacter, Enterococcus, Erwinia, Erysipelothrix, Escherichia, Eubacterium, Ewingella, Exiguobacterium, Facklamia, Filifactor, Flavimonas, Flavobacterium, Francisella, Fusobacterium, Gardnerella, Gemella, Globicatella, Gordona, Haemophilus, Hafnia, Helicobacter, Helococcus, Holdemania Ignavigranum, Johnsonella, Kingella, Klebsiella, Kocuria, Koserella, Kurthia, Kytococcus, Lactobacillus, Lactococcus, Lautropia, Leclercia, Legionella, Leminorella, Leptospira, Leptotrichia, Leuconostoc, Listeria, Listonella, Megasphaera, Methylobacterium, Microbacterium, Micrococcus, Mitsuokella, Mobiluncus, Moellerella, Moraxella, Morganella, Mycobacterium, Mycoplasma, Myroides, Neisseria, Nocardia, Nocardiopsis, Ochrobactrum, Oeskovia, Oligella, Orientia, Paenibacillus, Pantoea, Parachlamydia, Pasteurella, Pediococcus, Peptococcus, Peptostreptococcus, Photobacterium, Photorhabdus, Phytoplasma, Plesiomonas, Porphyrimonas, Prevotella, Propionibacterium, Proteus, Providencia, Pseudomonas, Pseudonocardia, Pseudoramibacter, Psychrobacter, Rahnella, Ralstonia, Rhodococcus, Rickettsia Rochalimaea Roseomonas, Rothia, Ruminococcus, Salmonella, Selenomonas, Serpulina, Serratia, Shewenella, Shigella, Simkania, Slackia, Sphingobacterium, Sphingomonas, Spirillum, Spiroplasma, Staphylococcus, Stenotrophomonas, Stomatococcus, Streptobacillus, Streptococcus, Streptomyces, Succinivibrio, Sutterella, Suttonella, Tatumella, Tissierella, Trabulsiella, Treponema, Tropheryma, Tsakamurella, Turicella, Ureaplasma, Vagococcus, Veillonella, Vibrio, Weeksella, Wolinella, Xanthomonas, Xenorhabdus, Yersinia,* and *Yokenella.* Other examples of bacterium include *Mycobacterium tuberculosis, M. bovis, M. typhimurium, M. bovis* strain BCG, BCG substrains, *M. avium, M. intracellulare, M. africanum, M. kansasii, M. marinum, M. ulcerans, M. avium* subspecies *paratuberculosis, Staphylococcus aureus, Staphylococcus epidermidis, Staphylococcus equi, Streptococcus pyogenes, Streptococcus agalactiae, Listeria monocytogenes, Listeria ivanovii, Bacillus anthraces, B. subtilis, Nocardia asteroides,* and other *Nocardia* species, *Streptococcus viridans* group, *Peptococcus* species, *Peptostreptococcus* species, *Actinomyces israelii* and other *Actinomyces* species, and *Propionibacterium acnes, Clostridium tetani, Clostridium botulinum,* other *Clostridium* species, *Pseudomonas aeruginosa,* other *Pseudomonas* species, *Campylobacter* species, *Vibrio cholera, Ehrlichia* species, *Actinobacillus pleuropneumoniae, Pasteurella haemolytica, Pasteurella multocida,* other *Pasteurella* species, *Legionella pneumophila,* other *Legionella* species, *Salmonella typhi,* other *Salmonella* species, *Shigella* species *Brucella abortus,* other *Brucella* species, *Chlamydi trachomatis, Chlamydia psittaci, Coxiella burnetti, Escherichia coli, Neiserria meningitidis, Neiserria gonorrhea, Haemophilus influenzae, Haemophilus ducreyi,* other *Hemophilus* species, *Yersinia pestis, Yersinia enterolitica,* other *Yersinia* species, *Escherichia coli, E. hirae* and other *Escherichia* species, as well as other *Enterobacteria, Brucella abortus* and other *Brucella* species, *Burkholderia cepacia, Burkholderia pseudomallei, Francisella tularensis, Bacteroides fragilis, Fudobascterium nucleatum, Provetella* species, and *Cowdria ruminantium,* or any strain or variant thereof. The Gram-positive bacteria may include, but is not limited to, Gram positive Cocci (e.g., *Streptococcus, Staphylococcus,* and *Enterococcus*). The Gram-negative bacteria may include, but is not limited to, Gram negative rods (e.g., Bacteroidaceae, Enterobacteriaceae, Vibrionaceae, Pasteurellae and Pseudomonadaceae). In an embodiment, the bacteria can include *Mycoplasma pneumoniae.*

The term "protozoan" as used herein includes, without limitations flagellates (e.g., *Giardia lamblia*), amoeboids (e.g., *Entamoeba histolitica*), and sporozoans (e.g., *Plasmodium knowlesi*) as well as ciliates (e.g., *B. coli*). Protozoan can include, but it is not limited to, *Entamoeba coli, Enta-*

*moeabe histolitica, Iodoamoeba buetschlii, Chilomastix meslini, Trichomonas vaginalis, Pentatrichomonas homini, Plasmodium vivax, Leishmania braziliensis, Trypanosoma cruzi, Trypanosoma brucei,* and *Myxoporidia.*

The term "algae" as used herein includes, without limitations microalgae and filamentous algae such as *Anacystis nidulans, Scenedesmus* sp., *Chlamydomonas* sp., *Clorella* sp., *Dunaliella* sp., *Euglena so., Prymnesium* sp., *Porphyridium* sp., *Synechoccus* sp., *Botryococcus braunii, Crypthecodinium cohnii, Cylindrotheca* sp., *Microcystis* sp., *Isochrysis* sp., *Monallanthus salina, M. minutum, Nannochloris* sp., *Nannochloropsis* sp., *Neochloris oleoabundans, Nitzschia* Sp., *Phaeodactylum tricornutum, Schizochytrium* sp., *Senedesmus obliquus,* and *Tetraselmis sueica* as well as algae belonging to any of *Spirogyra, Cladophora, Vaucheria, Pithophora* and *Enteromorpha* genera.

The term "fungi" as used herein includes, without limitations, a plurality of organisms such as molds, mildews and rusts and include species in the *Penicillium, Aspergillus, Acremonium, Cladosporium, Fusarium, Mucor, Nerospora, Rhizopus, Tricophyton, Botryotinia, Phytophthora, Ophiostoma, Magnaporthe, Stachybotrys* and *Uredinalis* genera.

Discussion:

The present invention relates to, inter alia, a composition including a dielectric-silver nanocomposite material, methods of preparing and using such compositions. In one aspect, and as described above, metallic silver and silver-containing products have been found to be potent antibacterial agents, with an enhanced antibacterial efficacy relative to that of commonly used disinfectants, such as, sodium hypochlorite and phenol. Owing to its enhanced antibacterial properties, there is a continuing demand to utilize silver (for instance, either as a silver nanoparticle or in ionic form) as an antimicrobial agent as well. For instance, ionic silver (e.g. ($Ag^+$) ions) has been found to have low toxicity to human cells. In comparison with traditional antibiotics, silver ions are shown to be more effective against a number of microorganisms including fungi, viruses, and bacteria. This may be due to the fact that these microorganisms develop low resistance against silver ($Ag^+$) ions.

As the advances in biological applications of silver continue to increase, it may be desirable to increase loading efficiency of silver (for instance, either as silver nanoparticles or ionic silver) within a delivery matrix. This increase in the loading efficiency of silver within the delivery matrix, for instance, facilitates enhancing the chemical and the thermal stabilities of silver disposed therein. Advantageously, such enhanced stabilities of silver, in turn, allow a sustained release of the silver nanoparticle from the delivery matrix, thereby facilitating a sustained and prolonged increase in its antimicrobial efficacy. As known, silver ions have traditionally been loaded onto organic polymeric materials, such as, poly (L-lactide) fibers, for instance, during the fabrication of certain thermoplastic-based products that require high-temperature (e.g. >300° C.) processing conditions. In such cases, dielectric materials such as, silica, may also be employed as an attractive alternative to the traditional organic polymer materials, owing to their chemical inertness and outstanding thermal stability. Further, the dielectric materials, such as, silica matrix, are also considered as biocompatible and environmentally-friendly materials.

Disclosed herein, in part, is a composition that includes a dielectric-silver nanocomposite material in which a silver nanoparticle that has been co-loaded with ionic silver is encapsulated within a dielectric material, such as, for instance, silica material. In one aspect, the dielectric-silver nanocomposite material can be formed either as a nanoparticle (referred to herein as a "dielectric-silver nanocomposite particle") or as a gel-like matrix (referred to herein as "dielectric-silver nanocomposite gel"). In such an embodiment, the silver (for instance, silver from either the silver nanoparticle and/or the ionic silver) chelates with a silica matrix surrounding each of the silver nanoparticle and the ionic silver which, for instance, results in immobilizing the trapped silver. Note that, as used herein "dielectric material" refers to a material such as, silicon dioxide or any dielectric material with a dielectric constant K greater than about 3.9 (note that K=3.9 for $SiO_2$) that can chelate with silver, either in its nanoparticle form and/or ionic form. In the present disclosure, the dielectric material refers to silicon dioxide (referred to herein as "silica") for ease of understanding. Further, such an immobilization of silver, advantageously, minimizes or inhibits electronic oscillations of the valence electrons of the trapped silver, resulting in shifting the plasmon resonance out of the visible region (i.e., from 390 nm to 500 nm), thereby rendering the dielectric-silver nanocomposite material (referred to herein as "silica-silver nanocomposite particle") transparent. Additionally, a sustained release of silver, for example, as a silver nanoparticle and/or ionic silver, facilitates the silica-silver nanocomposite material/particle to function as an antimicrobial agent that eliminates and/or inhibits the formation of microbes over surfaces. In one example, the antimicrobial characteristics of the composition that includes the silica-silver nanocomposite material/particle may be such that the composition may eliminate and/or kill about 70% to about 99% of microbes, or minimize the growth of microbes from a surface by an order of about 70% to about 99% relative to that of an untreated surface.

By way of example, the composition including the silica-silver nanocomposite material/particle can also be used as an antimicrobial coating over surfaces of structures, such as, but are not limited to, textile fabrics, cooking counters, food processing facilities (e.g., food, meat, poultry and the like), airplane interiors, kitchen utensils, food packaging materials, swimming pools, metals (e.g., metal oxides, metal alloys and the like), drug vials, medical instruments, medical implants, yarns, fibers, gloves, furniture, plastic devices (including, for instance, polymer and/or polymer blends), toys, diapers, leather, tiles, filters or filtration units (e.g., HEPA for air and water), glass or glass like structures, flooring metals (e.g., stone, ceramic, marble, granite and the like) and the combination thereof.

In exemplary embodiment, the silica-silver nanocomposite material/particle may be synthesized as illustrated in FIG. 1. As one skilled in the art will understand, the reaction process discussed below can be performed using a single reaction vessel or can use multiple reaction vessels. By way of an example, a capping-agent precursor (not shown) is dissolved in an aqueous solution and chilled to approximately 0° C. The aqueous solution of the capping-agent precursor is agitated till a clear solution is obtained, to which an aqueous solution of silver-precursor is added and the reaction mixture is further agitated until dissolved. A freshly prepared solution of a reducing agent in deionized water is added to the above mixture at 0° C. and stirred vigorously. A rapid color change of the reaction mixture is observed from an initial transparent solution to translucent dark yellow solution, followed by a gradual color change to transparent brilliant yellow solution indicating a progression in the reaction process. The reaction mixture was then allowed to stir for 2 hours at 0° C. till completion of the reaction, resulting in the formation of a capping-agent coated silver nanoparticle (referred to herein as "silver nanoparticle"). Although not intending to be bound by theory, ionic silver in the form of excess silver-precursor may also be present along with the silver nanoparticle in the reaction mixture. Examples of capping-agent precursor may be or include, but are not limited to, citric acid, or a citrate salt thereof, and the examples of silver-precursor may include, but are not limited to, silver nitrate salt, a silver chelate (e.g., chelating agent such as, p-dimethylaminobenzalrhodanine, tris(phenanthroline) Fe(II) and the like, and thiol silver complexing chelates (mercaptans, such as, dimethylsulfoniopropanoate, mercaptomethane and the like)).

By way of an example, and in one embodiment, a silver nanoparticle (i.e., citrate-coated silver nanoparticle) has been synthesized using a borohydride reduction method in which silver ions are reduced to metallic silver which, for instance, undergoes a nucleation process by aggregating each of the metallic silver particles, followed by a growth process to form silver nanoparticles. In one example, the formation of the silver nanoparticles may be summarized, as depicted in FIG. 14.

Figure 2:
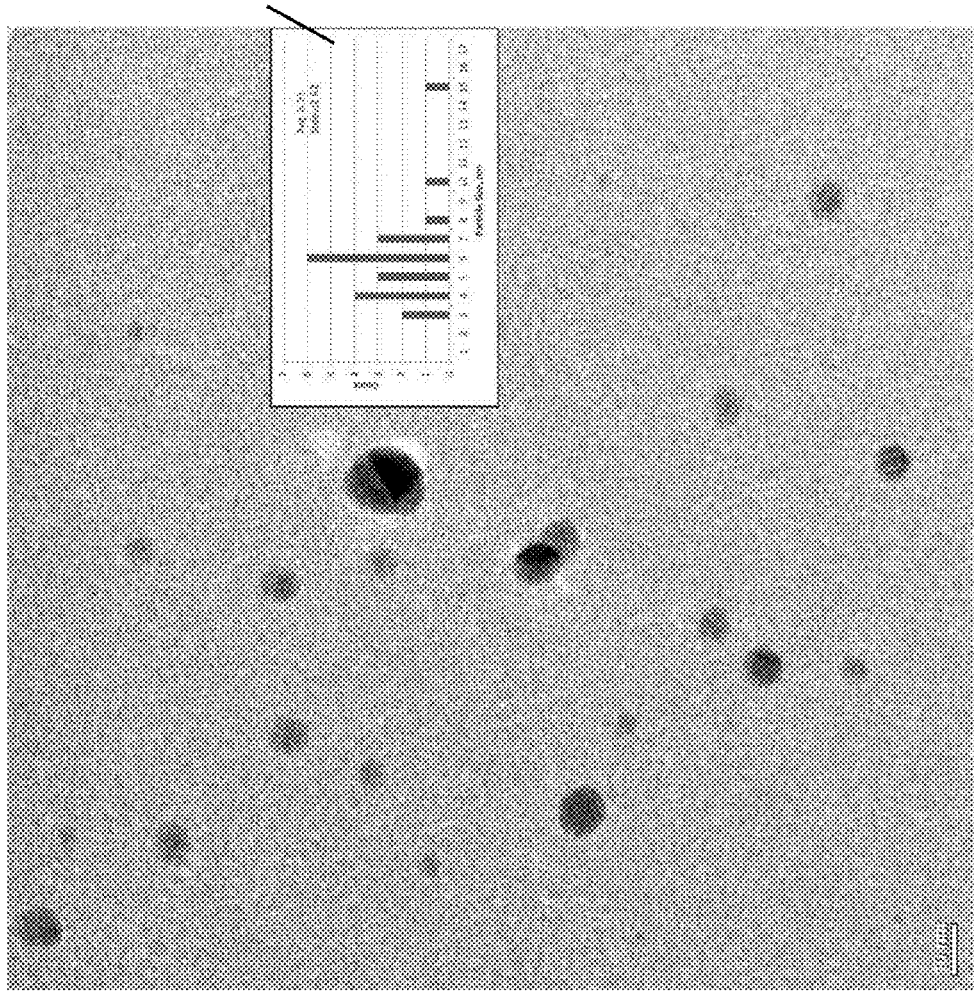
FIGS. 2A-2B illustrate one example of a transmission electron micrograph (TEM) of the silver nanoparticle, prior to the coating with a silica matrix, and shows particle size distribution of each of the citrate-coated silver nanoparticle, in accordance with one or more aspects of the present invention.
Figure 3:
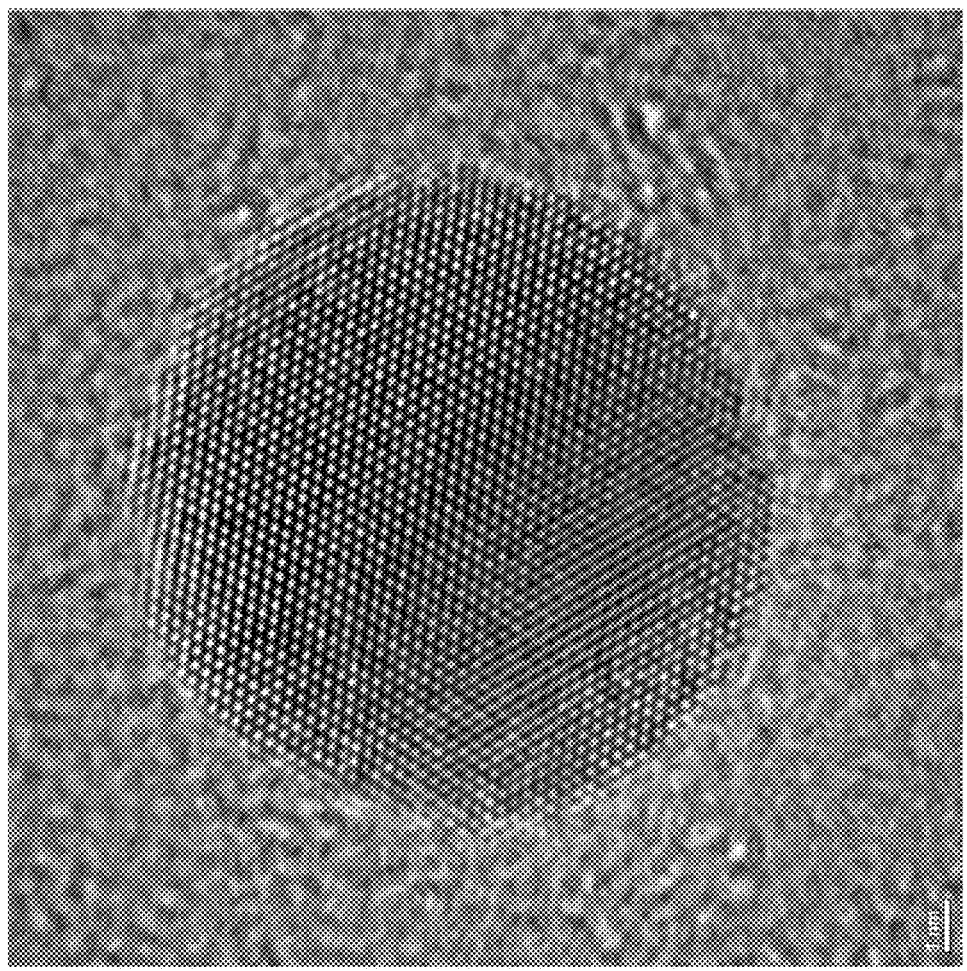
FIGS. 3 illustrates another example transmission electron micrograph (TEM) of the citrate-coated silver nanoparticle, prior to the coating with the silver matrix, and shows crystalline lattice structure of the silver nanoparticle, in accordance with one or more aspects of the present invention.

The size and the diameter of each of the silver nanoparticles can be controlled during the nucleation process by using the capping-agent, such as, citrate, during the borohydride reduction method. Advantageously, the citrate capping-agent adsorbs/coats a surface of each of the silver nanoparticles which, for instance, allows controlling the nucleation process, thereby controlling the particle size of each of the silver nanoparticle. Further, in one embodiment, the size and the diameter of each of the silver nanoparticles can be varied and controlled by adjusting parameters, such as, ratios of the silver precursor and the capping-agent precursor, polarity of the reaction medium, time of reaction, and the like. In one example, each silver nanoparticle may have a diameter within a range of about 3 nm to about 15 nm. In a specific example, each of the silver nanoparticles has a diameter of about 6 nm, as verified using transmission electron micrograph (TEM) image and imageJ software for analysis of the silver nanoparticles. For instance, as depicted in FIGS. 2A-2B, each of the citrate-coated silver nanoparticles have been found to be spherical in shape, and an estimation of size distribution of each of the citrate-coated silver nanoparticles has been obtained by measuring the diameter of the particles in the TEM image. As depicted in FIG. 2B, the average size of the citrate-coated silver nanoparticles has been calculated to be about 6. 51 nm, with a standard deviation of about 2.62 nm. Further, the silver nanoparticles may have a crystalline lattice structure (for instance, a face-centered cubic configuration) as indicated by the regularity of constructive and destructive interferences forming the TEM image depicted in FIG. 3.

Figure 4:
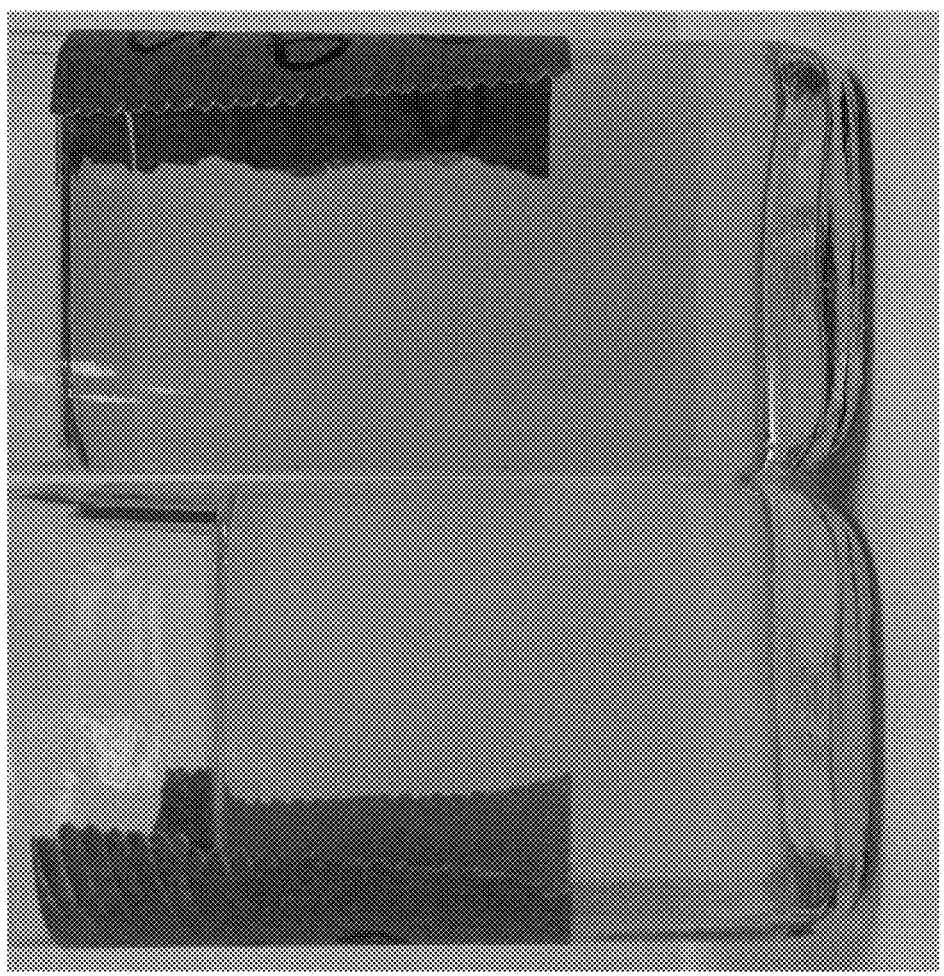
FIG. 4 illustrates one example of a visual confirmation of successful coating of silver nanoparticle and silver ions with silica matrix, as evident by a change in color of a solution containing silica-silver nanocomposite particle, prior to and subsequent to the addition of ammonium hydroxide ($NH_4OH$), in accordance with one or more aspects of the present invention.

Continuing further with FIG. 1, the silver nanoparticle that has been coated with the capping agent and any of the remaining unreacted silver ions are then incorporated into the silica nanoparticles, for instance, employing a Stober synthesis mechanism, using an inorganic base in presence of an organic solvent, resulting in a silica-silver nanocomposite particle, in accordance with one or more aspects of the present invention. By way of example, the silica-coated silver nanocomposite particle may be formed by further diluting the silver nanoparticle that has been coated with capping agent to form an aqueous solution, to which a dielectric-material precursor in an organic solvent, such as, ethanol, is added and stirred at room temperature. By way of example, the dielectric-material precursor may be or include, a silane precursor such as, for example, a silane compound (e.g., alkyl silane, tetraethoxysilane (TEOS), tetramethoxysilane, sodium silicate, or any silane precursor that can produce silicic acid or silicic acid like intermediates and a combination of these silane compounds). To initiate the coating reaction, an inorganic base, such as, ammonium hydroxide ($NH_4OH$) is added and the reaction mixture is allowed to stir at room temperature for a period of about 12 to 15 hours, i.e., overnight. After about 12 to 15 hours, an excess dielectric-material precursor may be added to the reaction mixture so as to coat any unreacted silver nanoparticle (i.e., citrate-coated silver nanoparticle) and the ionic silver. As the reaction progresses, an initial yellow color of the solution is converted to a milky white solution, indicating successful coating of the silver nanoparticles and the ionic silver, as confirmed by the solutions depicted in FIG. 4. As depicted, FIG. 4 reveals the visual confirmation of successful coating as observed by a change in the color of the solution containing silica-silver nanocomposite particle, before and after the addition of $NH_4OH$. Note that, although not described in detail, in one example, one skilled in the art will understand that various analytical techniques, such as, Scanning Electron Microscopy (SEM) and Atomic Force Microscopy (AFM) techniques may be employed to image the silver-silica nanocomposite material. In such an example, both of these techniques will provide surface topography (also referred to as "surface morphology") of the particles. In another example, Scanning Electron Microscopy-Energy Dispersive Spectroscopy (SEM-EDS and/or SEM-EDAX) may also be employed to estimate elemental composition (i.e., percentage of silica to silver).

In one embodiment, and as described above, the silica-silver nanocomposite material may be obtained either as a nanoparticle or a gel-like matrix, depending upon the reaction conditions employed. In one example, the silica-silver nanocomposite material obtained as a nanoparticle may include, for instance, a silver nanoparticle being formed as a core component and the silica matrix surrounding the silver nanoparticle being formed as a corresponding shell component. In such an example, the silver ions may be interspersed within the shell component and surrounding the silver nanoparticle core component. As one skilled in the art will understand, and in another example, the silica-silver nanocomposite material obtained as a gel-like matrix may include, for instance, silica particles being interconnected to one another as an amorphous gel. In such an example, the silver nanoparticles and the silver ions may be interspersed randomly within the gel-like silica matrix and/or attached to one or more silica particles. As understood, the amorphous silica gel has no defined structure, unlike its crystalline counterpart, and may have amorphous structural composition. In one embodiment, the average size of the silica particles has been found to be about 30 nm.

By way of an example, the solution containing the silica-silver nanocomposite material may further be subjected to lyophilization, to obtain the silica-silver nanocomposite particle. As used herein, the "lyophilization" refers to a dehydration process in which moisture and/or other organic volatile solvents, such as, ethanol, amines, etc., are removed from the silica-silver nanocomposite particle by freezing the particle under vacuum, without damaging its crystallinity. Note that the citrate that is adsorbed over the surface of the silver nanoparticle may also be removed from the silica-silver nanocomposite particle. Alternatively, even if the citrate is present, it has been found to be non-selective to the antimicrobial characteristics and/or transparency of the silica-silver nanocomposite particle, as evident from the various experimental analyses of the silica-silver nanocomposite particle. The silver nanoparticle, during the lyophilization process, forms a white powder, while the silica-silver nanocomposite particle forms a slightly-off white powder. In one example, the diameter of each particle of the silica-silver nanocomposite particle may be within a range of about 2 nm to about 50 nm. In a specific example, each particle of the silica-silver nanocomposite particle has a diameter of about 2 nm (see FIG. 5B), as confirmed by its transmission electron micrograph (TEM) image depicted in FIGS. 5A-5B.

Note that there is a decrease in the size of the silver nanoparticle, prior to and subsequent to being coated with the silica matrix. This decrease in the size of each particle of the silver nanoparticle may be attributed to the formation of a silver-amine complex obtained during the silica coating step, and subsequent deposition of the silver into the silica matrix during lyophilization, for instance, resulting in redistributing the overall silver content without any significant loss of the silver. The size and the diameter of each particle of the silica-silver nanocomposite particle can be varied from a few nanometers to hundreds of nanometers by appropriately adjusting synthesis parameters, such as, amounts of silane precursor, polarity of the reaction medium, pH, time of reaction and the like. In one embodiment, silver present in the silica-silver nanocomposite particle may be within a range of about 1000 ng/mL to about 25000 ng/mL by weight percent of the silica-silver nanocomposite particle. In a specific example, silver present in the silica-silver nanocomposite particle may be about 2500 ng/mL. In one embodiment, the concentration of silver, subsequent to lyophilization and reconstitution, within the silica-silver nanocomposite particle has mathematically been found to be about 25.4 µg/mL.

Figures 5A, 5B:
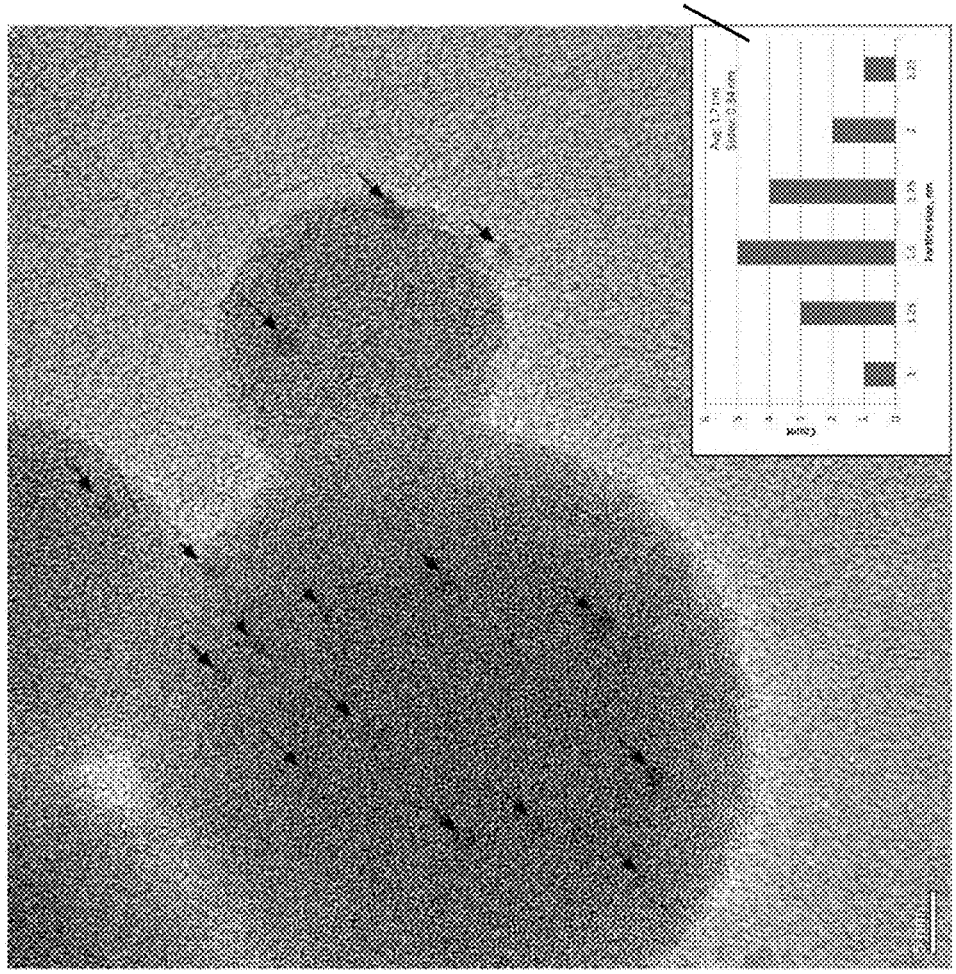
FIGS. 5A-5B illustrates another example transmission electron micrograph (TEM) of the silver nanoparticle and silver ions present within the silica-silver nanocomposite material, and shows increased electron density to further confirm the presence of each of the silver nanoparticle and the ionic silver, in accordance with one or more aspects of the present invention.
Figures 6A, 6B:
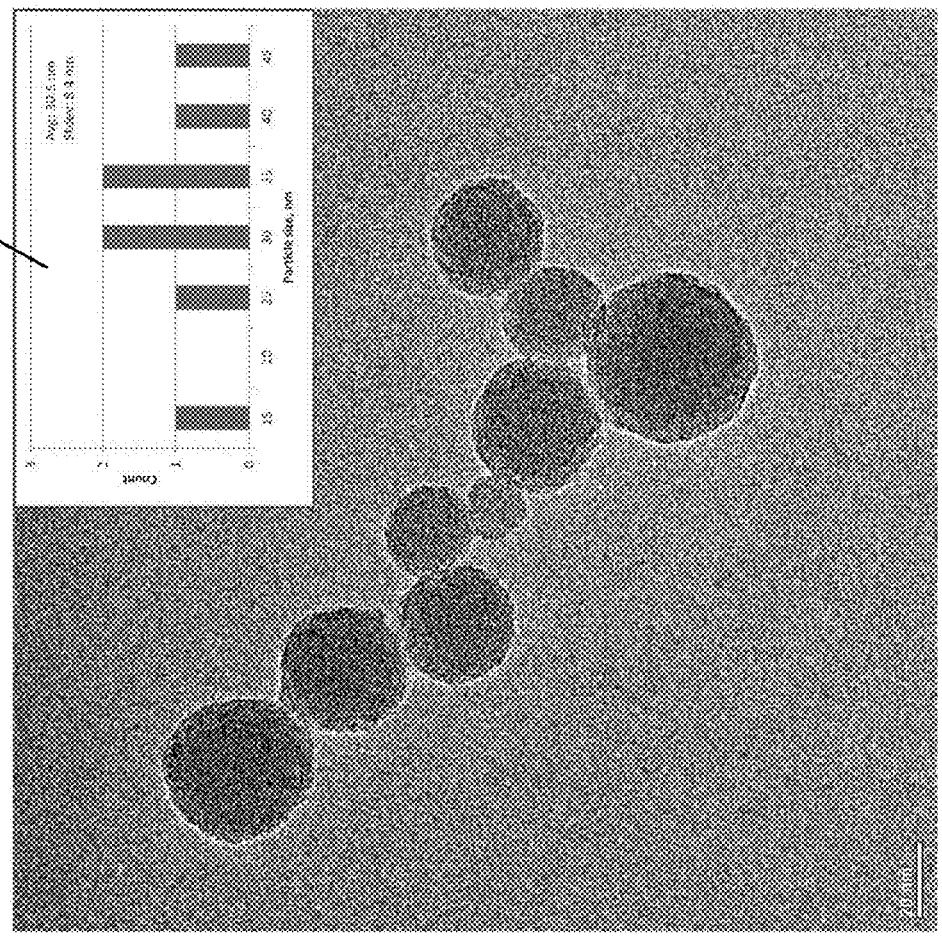
FIGS. 6A-6B illustrates another example transmission electron micrograph (TEM) of the silver nanoparticle present within the silica-silver nanocomposite material, and reveals spherical morphology of the silver nanoparticle disposed therein, in accordance with one or more aspects of the present invention.

As further revealed by the TEM image of FIGS. 5A-5B, an increase in the electron density (for instance, indicated by the dark spots in the TEM image) confirms the presence of the silver ions along with the silver nanoparticles. Note that, in one embodiment, the concentration of the silver ions may also be controlled by appropriately adjusting the synthesis parameters, such as, amounts of silane precursor, polarity of the reaction medium, pH, time of reaction and the like. The TEM image of FIGS. 5A-5B additionally reveals the crystalline structure of the silver nanoparticle disposed within the silica-silver nanocomposite particle. Still further, the TEM image of the silica-silver nanocomposite particle reveals the presence of the silver nanoparticle along with the ionic silver indicated by the spherical morphology, depicted in FIGS. 6A-6B.

Figure 7A:
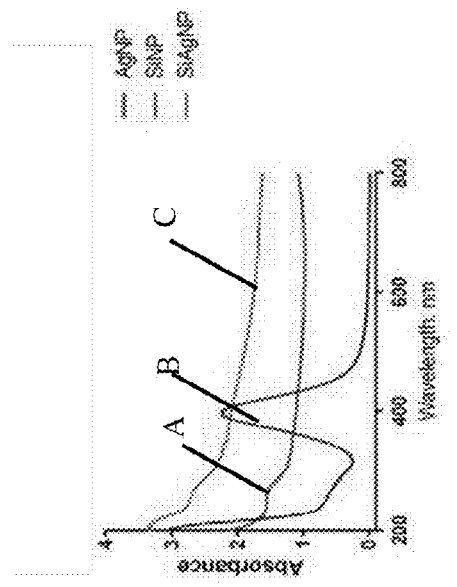
FIGS. 7A-7D depict representative spectrograms obtained by UV-Visible spectroscopic analysis of the dielectric-silver nanocomposite material, (and in particular, silica-silver nanocomposite material) comparable to those of a silver nanoparticle lacking a silica matrix, and a silica nanoparticle lacking the silver nanoparticle, respectively, in accordance with one or more aspects of the present invention.
Figure 7B:
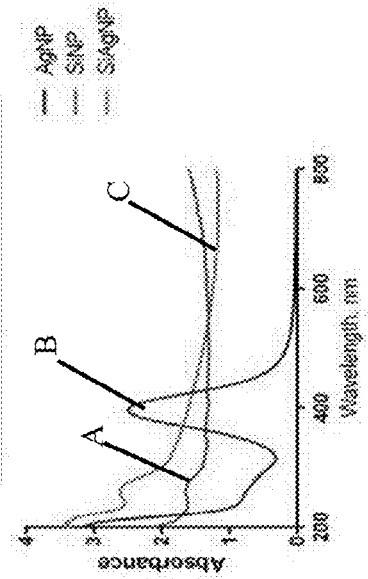
Figure 7C:
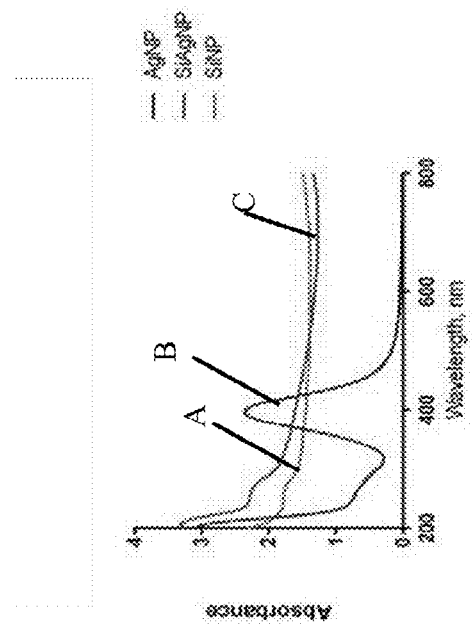
Figure 7D:
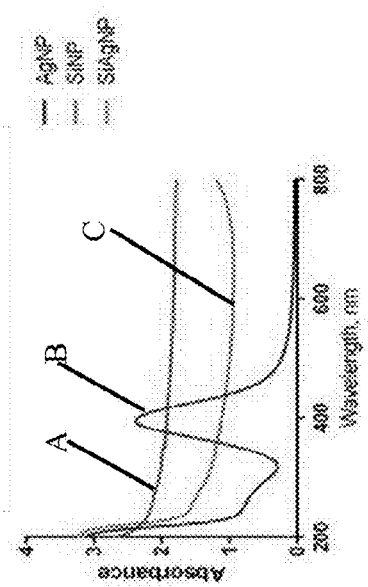

Further, in one aspect of the present invention, the silica-silver nanocomposite material, either as a nanoparticle or a gel-like matrix, has been observed to be transparent and colorless. As one skilled in the art will understand, metals, such as, silver, absorb light by creating plasmons, which are particle-like collective excitations of conduction electrons at a metallic surface, that, for instance, can be confirmed by corresponding signals and/or peaks in UV-Visible spectroscopic analysis thereof. A UV-Visible spectroscopic analysis of the silica-silver nanocomposite material, as depicted in FIGS. 7A-7D, has been performed with silver nanoparticle lacking the silica matrix and the silica nanoparticle lacking the silver components, respectively, as controls. Each of the samples, for instance, has same concentrations of silver (if present). By way of example, each of the silver nanoparticle, the silica-silver nanocomposite material and the silica nanoparticle have been prepared in three separate batches on three separate days in order to verify the robustness of the protocol, and the UV-Visible spectra of each of the samples have been analyzed, as depicted in FIGS. 7B-7D, while the UV-Visible spectrum, as depicted in FIG. 7A, reveals an average spectrum of the corresponding materials.

As evident, the absence of the silver plasmon peak in the UV-visible spectrum of the silica-silver nanocomposite particle (C) relative to the presence of the peak centered at 398 nm for the silver nanoparticle (B) confirms a successful coating of the silver nanoparticle and the silver ions with silica matrix. Such successful coating of the silver nanoparticle and the silver ions with silica, in turn, could result in silver, from each of the silver nanoparticles and the ionic silver, for instance, being chelated by the silanol (Si—OH) groups present in the silica matrix to form a weak Ag—Si complex. Advantageously, the chelation of silver by the silanol groups results in immobilizing silver from both the silver nanoparticles and the silver ions; thereby minimizing or inhibiting electronic oscillations of the valence electrons of the trapped silver. This, for instance, results in shifting the plasmon resonance (i.e., blue shifting the plasmon) out of the visible region (i.e., from 390 nm to 500 nm) and also rendering the silica-silver nanocomposite particle transparent. As used herein, the "blue shifting of the plasmon" refers to a spectral shift towards lower wavelengths (i.e., higher energy and higher frequency) as confirmed by the absence of the silver plasmon peak in the UV-Visible spectrum depicted in FIGS. 7A-7D. This observation is also consistent with the absence of the silver peak in the UV-Visible spectrum of the silica nanoparticle (A) lacking the silver components. As understood, the shift in the plasmon peak, in one embodiment, could depend on the thickness of the silica material encapsulating the silver nanoparticles and the silver ions of the silica-silver nanocomposite particle. Note that, as described above, the presence of the silver nanoparticle and the silver ions in the silica-silver nanocomposite particle has been confirmed by the TEM images, as depicted in FIGS. 5A-5B and FIGS. 6A-6B.

Figure 8:
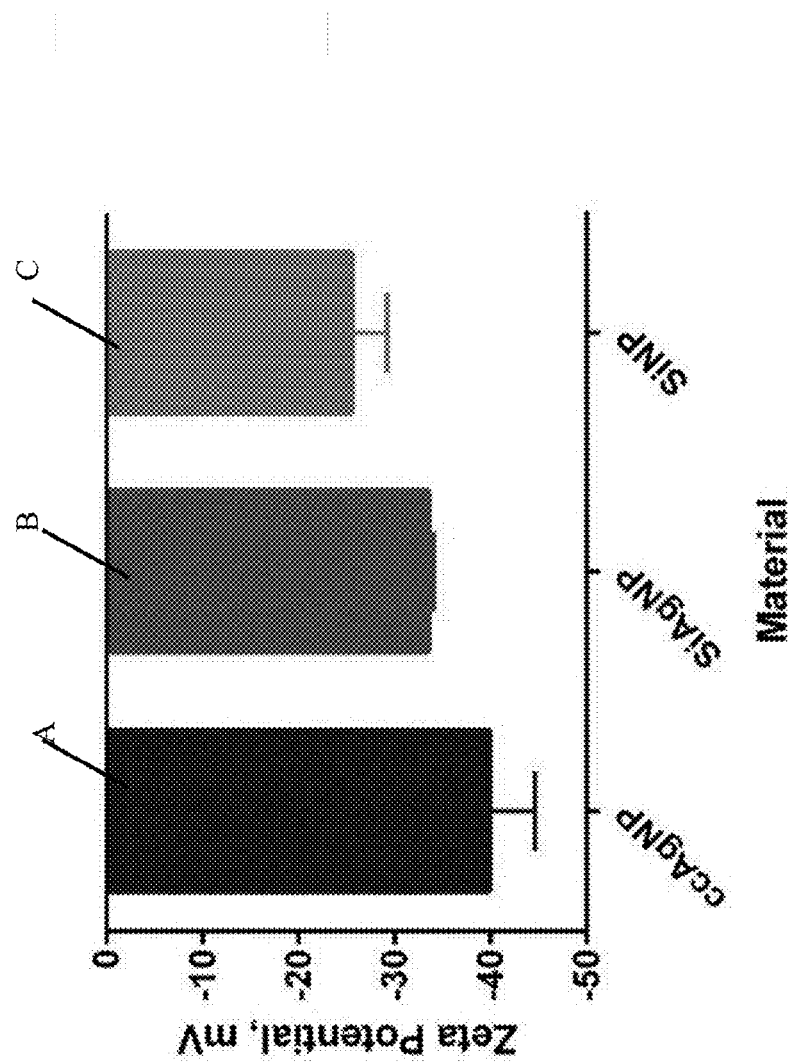
FIG. 8 depicts representative example of Zeta potential of the silica-silver nanocomposite material relative to that of the silver nanoparticle lacking the silica matrix and the silica nanoparticle, respectively, in accordance with one or more aspects of the present invention.

Additionally, the successful coating of the silver nanoparticle and the silver ions by the silica matrix is further confirmed by a difference in zeta potentials of the silica-silver nanoparticle (SiAgNP) and silica nanoparticle (SiNP), depicted in FIG. 8. As used herein, "Zeta potential" refers to the potential difference existing between the surface of a solid particle immersed in a conducting liquid and the bulk of the liquid. Note that, as depicted in FIG. 8, Zeta potential of the silica-silver nanocomposite particle (B) lies between that of the silver nanoparticle and the silica nanoparticle, respectively. In a specific example, the Zeta potential of the silica-silver nanocomposite particle is within a range of about −30 mV to −40 mV. The Zeta potential, further, reveals a high degree of colloidal stability of the resultant silica-silver nanocomposite particle (SiAgNP).

Figure 9E:
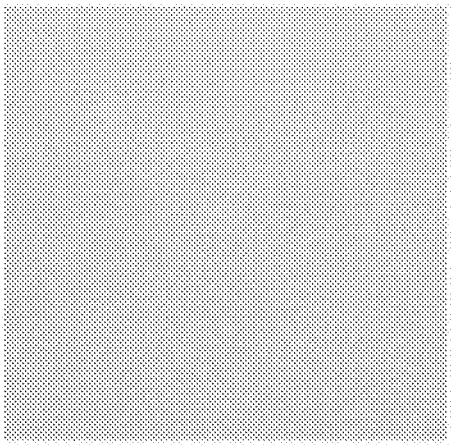
Figure 9F:
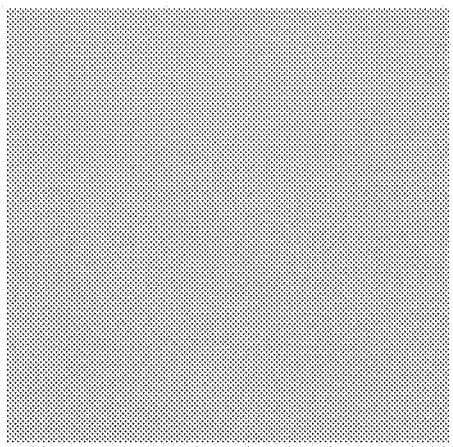
Figure 9G:
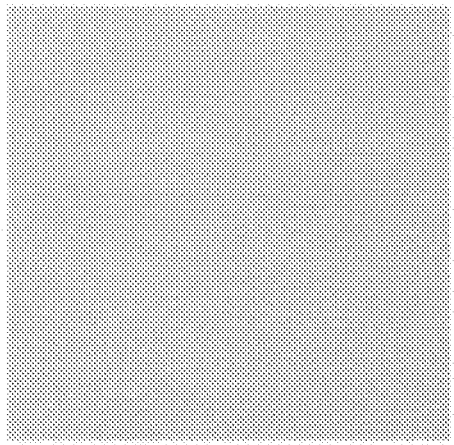
Figure 9H:
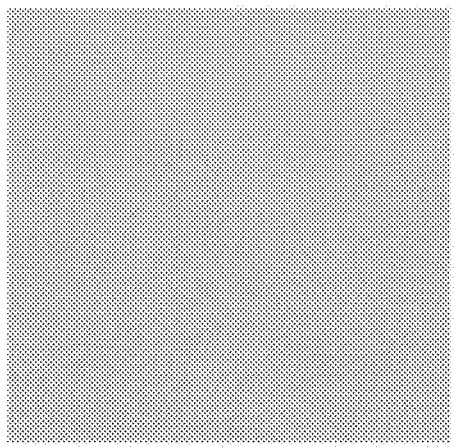

In an enhanced embodiment, color passivity of the silica-silver nanocomposite particle has been further confirmed by subjecting tiles that have been coated with the silica-silver nanocomposite particle to thermal and UV treatments, as depicted in FIGS. 9A-9H. In one embodiment, tiles, for instance, that have been coated with silver nitrate ($AgNO_3$) (see FIGS. 9A & 9B) and silver nanoparticle (AgNP) (see FIGS. 9C & 9D), have been used as controls, and have also been subjected to the thermal and the UV treatments, respectively. As evident, in FIGS. 9A & 9B, the tiles that have been coated with silver nitrate do not show formation of color before the thermal treatment (9A), and subsequent to the thermal treatment (9B), show a dark brown/black color. As depicted in FIGS. 9C & 9D, tiles coated with silver nanoparticle (AgNP) show formation of color immediately upon coating (FIG. 9C), and no noticeable change (FIG. 9D) after thermal and UV treatments, respectively. As evident in FIGS. 9E & 9F, tiles coated with silica nanoparticle (SiNP), which also have been used as a control, do not show formation of color before (FIG. 9E) or after (FIG. 9F) the thermal and UV treatments. Referring to FIGS. 9G & 9H, tiles coated with silica-silver nanocomposite particle (SiAgNP) shows no formation of color before (FIG. 9G) or after (FIG. 9H) the thermal and UV treatments.

Still further, in another embodiment of the present invention, the silica-silver nanocomposite particle has been observed to have enhanced antimicrobial efficacy relative to that of an isolated silver nanoparticle lacking the dielectric material encapsulation. Such an enhanced antimicrobial efficacy, for instance, may be attributed to a sustained release of silver, for example, either as a nanoparticle and/or its ionic form. By way of example, antimicrobial efficacy of the silica-silver nanocomposite particle was evaluated relative to that of the silver nanoparticle (AgNP) lacking the dielectric material encapsulation and aqueous silver nitrate (AgNO$_3$) solutions, respectively, at equivalent concentrations of silver (if present). Note that, the silver nanoparticle and the silver nitrate, in this example, have been used as a positive growth control, while the silica nanoparticle (SiNP) lacking silver components, has been used as a negative growth control. Further antimicrobial characterization of the silica-silver nanocomposite particle, for instance, using a bacterial viability assay revealed a time-dependent killing trend in the silica-silver nanocomposite particle (SiAgNP) that suggests a controlled release of ionic silver (Ag$^+$) from within the silica matrix. Antimicrobial efficacy of the silica-silver nanocomposite particle SiAgNP was determined to lie between that silver nitrate (which, for instance, is a most effective antimicrobial form of silver) and that of silver nanoparticle (AgNP) (which, for instance, has a least effective antimicrobial form of silver).

By way of example, the antimicrobial efficacy of the silica-silver nanocomposite particle has been studied by subjecting the silica-silver nanocomposite particle to minimum inhibitory concentration (MIC) studies which, for instance, may be performed by exposing two normal human flora organisms, namely, a Gram Negative rod, such as, E. coli, that is commonly found in the gut, and a Gram Positive cocci, such as, S. aureus, found on skin surfaces, to the silica-silver nanocomposite particle over a period of time, i.e., for 1, 4, and 8 hours of exposure. Alamar Blue has been used as an indicator of microbial growth, and it has been determined that the efficacy of silica-silver nanocomposite particle (SiAgNP) increased with an increase in time of exposure, suggesting a gradual release of antimicrobial silver compounds. By way of example, FIGS. 10A-10C depict a graphical representation of the antimicrobial efficacy of the silica-silver nanocomposite particle with respect to Gram Positive cocci, such as, S. aureus over a period of time, i.e., for 1, 4 and 8 hours of exposure, respectively, while FIG. 10D depicts a graphical representation of the time of exposure and dosage-dependent killing trend of the silica-silver nanocomposite particle against the Gram Positive cocci (for example, S. aureus). As depicted in FIGS. 10A-10C, silver nanoparticle and silver nitrate were employed as positive growth controls, while silica nanoparticle has been used as negative growth control. Note that, as depicted in FIG. 10D, and in a specific example, the silica-silver nanocomposite particle having concentration of silver is about 0.050 µg/mL for about 8 hours of exposure to bacteria exhibits optimal antimicrobial efficacy against the Gram Positive cocci (for example, S. aureus). Note that, as depicted, due to availability of equipment, readings for S. aureus MIC studies were taken after 48 hours of incubation, leading to breakdown of Alamar Blue, as described in the literature. However, at higher concentrations of Ag, and as described below, it can be observed that the levels of reduction in colony-forming unit (CFU) never exceeded those of the positive growth control, indicating that microbial populations were controlled in the wells corresponding to concentrations greater than about 0.792 µg/mL.

By way of example, FIGS. 11A-11C depict a graphical representation of the antimicrobial efficacy of the silica-silver nanocomposite particle with respect to the Gram Negative rod, such as, E. Coli over a period of time, i.e., for 1, 4 and 8 hrs of exposure, respectively, while FIG. 11D depicts a graphical representation of the time of exposure and dosage-dependent killing trend of the silica-silver nanocomposite particle against the Gram Negative rod (for example, E. Coli). In this example, silver nanoparticle and silver nitrate were employed as positive growth controls, while silica nanoparticle was used as negative growth control, as similar to as described above in connection with FIGS. 10A-10C. It was determined that the novel material, silica-silver nanocomposite particle (SiAgNP), when tested against E. coli exhibits an antimicrobial efficacy which lies between that of the silver nanoparticle (AgNP), an initially metallic form of Ag, and silver nitrate (AgNO$_3$) solution, an initially ionic form of Ag, as evident from the FIGS. 11A-11C. As time of exposure is increased from 1 to 4 to 8 hours, the efficacy of the silica-silver nanocomposite particle (SiAgNP) approached the efficacy of AgNO$_3$. A similar conclusion can be drawn from testing using S. aureus, however higher quality data would allow for better analysis.

Figure 12B:
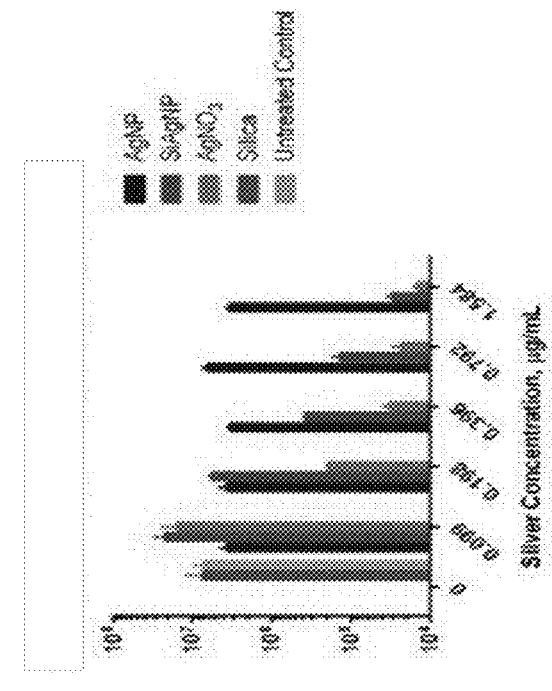
FIGS. 12A-12B show a graphical representation of one embodiment of a colony forming unit (CFU) study of the silica-silver nanocomposite material with respect to the Gram Positive cocci, (for example, *S. aureus*), in accordance with one or more aspects of the present invention.
Figure 12A:
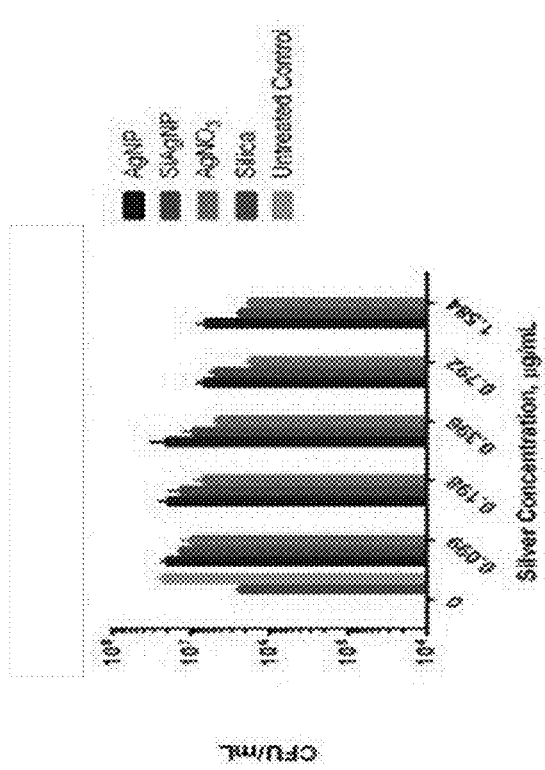

To better understand the antimicrobial effects of the material, a bacterial viability assay was carried out at silver (Ag) concentrations ranging from 0.725 to 0.05 µg/mL in each material, as well as undiluted silica nanoparticle (SiNP) for time points 1 and 4 hours, and as depicted in FIGS. 12A-12B and 13A-13D, respectively. By way of example, FIGS. 12A-12B depicts a graphical representation of a reduction in colony-forming units (CFU) of the Gram Positive cocci (for example, S. aureus) as observed at five concentrations of silver ranging from about 0.1 µg/mL to about 0.6 µg/mL. As depicted, the antimicrobial efficacy of the silica-silver nanocomposite particle consistently fell between that of the metallic silver (for example, AgNP) and the ionic silver (for instance, AgNO$_3$) upon exposure over a period of time, namely, 1 hour of exposure (FIG. 12A) and 4 hours of exposure (FIG. 12B), respectively. Similarly, FIGS. 13A-13D depicts a graphical representation of a reduction in colony-forming units (CFU) of the Gram Negative rod (for example, E. Coli) as observed at five concentration of silver ranging from about 0.1 µg/mL to about 0.6 µg/mL. As depicted, the reduction in the CFU has been measured upon exposure over a period of time, namely, 1 hour of exposure (FIG. 13A), 4 hours of exposure (FIG. 13B), respectively. Note that, the experiment has been repeated to prove the consistency, as depicted in FIG. 13C (which, for instance, has been exposed for 1 hr) and FIG. 13D (which, for instance, has been exposed for 4 hrs) respectively. These time points were selected by analyzing MIC data, and noting a pronounced change in reduction of Alamar Blue between 1 and 4 hours, while a much smaller change was noted from 4 to 8 hours of incubation. Ag concentrations were selected to include MICs for each material, allowing for comparison of relative efficacy.

96 well plates were prepared in an identical fashion to MIC studies for time points 1 and 4 hours, and incubated at 37° C. for the allotted time. After incubation, 10 µL samples were drawn off after thoroughly mixing each well, then diluted and spotted onto MH$_2$ agar plates as described above.

Plates were incubated at 37° C. for 12 to 14 hours, and observed for growth. Reduction of CFU for each material at the selected concentrations at each time point can be seen in FIGS. 12A-12B and 13A-13D.

EXAMPLES

Materials

Reagents used for synthesis were purchased from commercial vendors and used as received, with no additional purification. Silver nitrate ($AgNO_3$, obtained from Acros Organics), sodium borohydride ($NaBH_4$), and trisodium citrate (TSC, obtained from Fisher Biotech) were utilized in the synthesis of silver nanoparticles for testing. Tetraethyl orthosilicate (TEOS, obtained from Gelest Inc.), ammonium hydroxide ($NH_4OH$, obtained from Fisher), and 95% ethanol (EtOH, obtained from Fisher) were utilized in the coating of the synthesized silver nanoparticles. Muller Hinton II ($MH_2$) agar and broth were purchased from Fluka, and prepared as directed in the literature using a Tuttnauer EZ10 autoclave. 10× phosphate buffered saline was purchased from Life Technologies and diluted to 1× using deionized water (Nanopure; Barnstead Model #D11911), and filter sterilized using a 0.2 micron Nalgene filter. M9 minimal salts+1% glucose media was generated from M9 minimal salts (obtained from Sigma) and dextrose powder (obtained from Fluka) using deionized water, and filter sterilized using a 0.2 micron Nalgene filter. *Escherichia coli* (ATC C #10536) and *Staphylococcus aureus* (ATCC #25923) were purchased from the American Type Culture Collection and maintained on $MH_2$ agar plates for the following experiments, and grown for 12-14 hours in $MH_2$ broth prior to broth micro dilution testing. Alamar blue (obtained from Life Technologies, Cat #DA L1100) was utilized as received. Carbon coated 400 mesh copper TEM grids were purchased from Electron Microscope Sciences.

Example 1

Synthesis of Citrate-Coated Silver Nanoparticles

Citrate capped silver nanoparticles, having a concentration of silver of about 0.29 mM, were synthesized, using a borohydride reduction protocol. For each synthesis, a rectangular glass bottle, having a total volume approximately 120 mL, was washed with a small volume of acetone to remove manufacturing residues, and allowed to dry. About 100 mL of deionized water, at room temperature, was then placed in the bottle, to which about 31.2 mg trisodium citrate (TSC) was added. The bottle was shaken to dissolve the TSC and then chilled to approximately 0° Celsius, as indicated by the formation of small ice crystals in the solution. Further agitation was utilized until it was observed that the ice crystals were no longer visible. The chilled bottle was then placed in an ice bath on a stir plate, a small stir bar was added, setting to stir at approximately 800 rpm. Fresh silver nitrate solution having a molarity of about 5 mM was prepared using about 10 mL of room temperature $ddH_2O$ and about 8.5 mg silver nitrate powder, and shaken until dissolved. About 6.25 mL of this solution was added to the chilled, stirring TSC solution. Fresh sodium borohydride solution was mixed immediately before use by adding about 37.8 mg $NaBH_4$ to about 10 mL of room temperature deionized water, and shaking vigorously. About 625 µL of the $NaBH_4$ was then added at a rate of approximately 60 µL/30 seconds to the vigorously stirring 0° C. silver nitrate/TSC solution. A rapid initial color change from transparent and colorless to translucent dark yellow was observed, followed by a gradual color change to transparent brilliant yellow as the reaction progressed. After the entire volume, about 625 µL, of $NaBH_4$ solution was added, taking approximately 5 minutes, the reaction was left to stir for two hours at 0° C. After two hours, the bottle was transferred to a refrigerator at 4° C. for storage.

Example 2

Synthesis of Silica Coated Silver Nanoparticles (SiAgNP)

After synthesis, the citrate capped silver nanoparticles (AgNP) were diluted to a final concentration of about 0.24 mM by adding about 16.117 mL AgNP stock to about 3.519 mL $ddH_2O$. This stock solution was then added to about 79 mL of 95% ethanol, and placed on a stir plate at 400 rpm. The color of the solution was noted to be bright yellow. About 223 µL tetraethylorthosilicate (TEOS) was added and allowed to fully dissolve into the ethanol solution under stirring. To initiate the coating reaction, about 933 µL of $NH_4OH$ was added, and allowed to stir for about 12-15 hours (i.e., overnight). After stirring for about 12-15 hours, an additional 100 µL of TEOS was added, and allowed to stir for another 1 hour. An additional 100 µL of TEOS was then added and allowed to stir for 1 more hour. After synthesis, the initial yellow color of the solution was replaced by a milky white, indicating successful coating of the silver nanoparticles.

Example 3

Synthesis of Silica Nanoparticle (SiNP) Control Material

About 19.636 mL of $ddH_2O$ was added to 79 mL of 95% ethanol, and placed on a stir plate at 400 rpm. About 223 µL tetraethyl ortho silicate (TEOS) were added and allowed to fully dissolve into the ethanol solution under stirring. To initiate the reaction, about 933 µL of $NH_4OH$ was added, and allowed to stir for about 12-15 hours (i.e., overnight). After stirring for about 12-15 hours, an additional 100 µL of TEOS was added, and allowed to stir for another 1 hour. An additional 100 µL of TEOS was then added and allowed to stir for 1 more hour. After synthesis, the solution was noted to be transparent.

Example 4

Purification of Materials 10 mL aliquots of each of the silver nanoparticle (SiNP), and the silica-silver nanoparticle (SiAgNP) were placed into about 15 mL conical tubes and snap frozen in liquid nitrogen. The frozen samples were then lyophilized for approximately 12 hours (i.e., overnight) until only a fine white powder remained of each sample. Each sample was then reconstituted using about 2 mL $ddH_2O$, followed by sonication for approximately 5 minutes to break up the aggregates. The molarity of each of the samples with respect to silver was about 0.235 mM.

Example 5

Characterization of Materials

After synthesis and purification, each of the silver nanoparticles (AgNP), silica nanoparticles (SiNP) and silica-silver nanoparticle (SiAgNP) were characterized to establish the physical and antimicrobial properties of each, with a silver nitrate (AgNO$_3$) solution of equivalent silver concentration being used as a control.

Characterization of Physical Properties:

Example 6

UV-Visible Spectrophotometry

The absorbance spectrum of each material, i.e., silver nanoparticle (AgNP), silica nanoparticle (SiNP), silica-silver nanoparticle (SiAgNP) and silver nitrate (AgNO$_3$) was collected in the range of about 200 to about 800 nm at a bandwidth of about 0.5 nm, utilizing a Cary UV-Vis spectrophotometer. Two quartz cuvettes were used, with a water blank in the reference cell. An initial background subtraction was taken after zeroing the machine, and all samples were disbursed in ddH$_2$O for measurements at synthesized concentrations. Cuvettes were briefly sonicated immediately prior to measurements to minimize the presence of aggregates.

Example 7

Zeta Potential

10× diluted samples were loaded into polycarbonate folded zeta potential cells, and placed in the zeta potential machine. Experiment parameters regarding refractive index, extinction coefficient of the material being tested, and solvent viscosity were input, and testing was auto-optimized by the software. An average zeta potential value was calculated from the aggregated results of each run. The cell was flushed twice with approximately 5 mL of ddH$_2$O between each sample.

Example 8

Transmission Electron Microscopy (TEM)

TEM imaging was carried out on the silver nanoparticle AgNP and silica-silver nanoparticle SiAgNP. About 15 μL aliquots of freshly sonicated material was drop coated onto ultrathin carbon coated copper TEM grids, and allowed to dry for 1 hour at room conditions. TEM grids were then transferred to separate microcentrifuge tubes and placed under 0.024 mBar conditions for 1 hour to remove any trace water. Grids were stored overnight in ambient conditions prior to imaging studies.

Example 9

Color Passivation Study

White tiles were purchased from Home Depot, and scrubbed with acetone and Kim wipes to remove any oils which would inhibit materials from adhering well. After scrubbing and allowing the tiles to dry, about 50 μL samples of each material were spread over an area approximately 3cm by 3cm, and allowed to dry under ambient conditions. A picture was taken, and then tiles were exposed to long and shortwave UV radiation for 5 minutes, and briefly heated using a butane torch, and photographed again to observe the change in color of each material.

Characterization of Antimicrobial Properties

Example 10

Minimum Inhibitory Concentration (M IC) Study

MIC studies were carried out using broth microdilution in a 96 well plate format. Organisms were grown for 12 hours in 40 mL of MH2 broth at 37° C. on an orbital shaker in 50 mL conical tubes, loosely capped to allow gas exchange. Prior to testing, each organism was spun down at 4500 g for 3 minutes, and the supernatant discarded. The pellet was resuspended in 40 mL of warm M9/1% glucose broth and incubated further for 2 hours on the orbital shaker. While incubating in M 9/1% glucose media, plates were prepared by pipetting 100 μL M9/1% glucose into each well. Row A was then filled with 100 μL of each material in triplicate, AgNP, SiAgNP, AgNO$_3$, and serial diluted by transferring 100 μL of each row down one successive row until 8 dilutions were achieved. 100 μL were discarded from row H, leaving a total volume per well of 100 μL of broth and diluted antimicrobial agent. SiNP was treated similarly, but was diluted three times, utilizing columns 11 and 12. Positive and negative growth controls were included in triplicate in column 1. For each organism, 1 plate was prepared for each time point, 1 hour, 4 hours, and 8 hours.

After incubating each organism for two hours in M 9/1% glucose, the turbidity was adjusted to match a 0.5 MacFarland standard, corresponding to roughly 1.5×10$^8$ CFU/mL for testing purposes, using warm M9/1% glucose. 100 μL of 0.5 MacFarland standard organism was then pipetted into each well for testing, and incubated at 37° C. on an orbital shaker for the designated time. After incubation for the prescribed time, 10 μL of alamar blue was added to each well, and each plate was incubated a further 24 hours. End point readings of alamar blue were taken at 570/600 nm, and reduction relative to the positive growth control calculated. Plates containing *E. coli* were incubated 48 hours before reading, while *S. aureus* plates were incubated 24 hours, due to availability of the equipment.

Example 11

Bacterial Viability Assay (CFU Study)

In order to gain a better understanding of the antimicrobial efficacy of each material, we carried out a colony forming unit study over two time points, 1 and 4 hours. 96 well plates were prepared and incubated as described for M IC studies, and 10 μL samples from wells containing the concentrations of antimicrobial agents were taken at each time point. Each sample was then transferred to row A of a 96 well plate containing 90 μL sterile 1× PBS per well, for a final volume of 100 μL and dilution factor of 10$^{-1}$. 10 μL of row A was then transferred to row B, and this dilution was carried out a gradient of concentrations ranging from 10$^{-1}$ to 10$^{-8}$ were established. 10 μL were discarded from row H, leaving a total volume of 90 μL per well. MH$_2$ agar plates labeled by material and time point were then spotted with five 10 μL drops from each well at each concentration, allowed to dry in the sterile conditions of a biosafety cabinet, and then incubated 12-14 hours before colonies were counted. Colony counts were then used to calculate initial CFU/mL values for each well at each time point, based on dilution factor. Relative CFU reduction compared to positive growth controls over time was calculated using this data.

What is claimed is:

1. A composition comprising:
a dielectric-silver nanocomposite material, the dielectric-silver nanocomposite material comprising a silver nanoparticle that is co-loaded with an ionic silver, and a dielectric material encapsulating each of the silver nanoparticle and the ionic silver, the silver from each of the silver nanoparticle and the ionic silver having a first plasmon resonance;
wherein silver from each of the silver nanoparticle and the ionic silver chelates with a matrix of the dielectric material, such that the silver from each of the silver nanoparticle and the ionic silver has a second plasmon resonance upon chelation; and
wherein the second plasmon resonance is less than the first plasmon resonance such that the dielectric-silver nanocomposite material is colorless.

2. The composition of claim 1, wherein the dielectric material surrounding each of the silver nanoparticle and the ionic silver renders the dielectric-silver nanocomposite material transparent.

3. The composition of claim 1, wherein the dielectric-silver nanocomposite material is a dielectric-silver nanocomposite particle, and the ionic silver is an ionic silver of a plurality of silver ions, wherein each of the plurality of silver ions discretely surround the silver nanoparticle, and are dispersed homogenously within the matrix of the dielectric material.

4. The composition of claim 3, wherein the silver nanoparticle is a silver nanoparticle of a plurality of silver nanoparticles, and a capping agent adsorbs a surface of each of the plurality of silver nanoparticles, wherein the capping agent controls nucleation of each of the plurality of silver nanoparticles within the matrix of the dielectric material to inhibit aggregation thereof.

5. The composition of claim 3, wherein antimicrobial characteristic and color passivity of the dielectric-silver nanocomposite material is non-selective to the capping agent.

6. The composition of claim 3, wherein the dielectric-silver nanocomposite material is a dielectric-silver nanocomposite gel, wherein each of the plurality of silver ions and the plurality of silver nanoparticles are homogenously dispersed within the matrix of the dielectric material.

7. The composition of claim 1, wherein the silver nanoparticle is a sustained-release silver nanoparticle and the ionic silver is a sustained-release silver ion, wherein a sustained-release of each of the silver-nanoparticle and the ionic silver promotes antimicrobial characteristics, without affecting transparency of the dielectric-silver nanocomposite material.

8. The composition of claim 7, wherein the dielectric-silver nanocomposite material has a first antimicrobial minimal inhibitory concentration and an isolated silver nanoparticle lacking the dielectric material encapsulation has a second antimicrobial minimal inhibitory concentration, which is greater than the first microbial minimal inhibitory concentration.

9. The composition of claim 7, wherein the dielectric-silver nanocomposite material has a first antimicrobial minimal inhibitory concentration to at least one of Gram Positive cocci and a Gram Negative rod and an isolated silver nanoparticle lacking the dielectric material encapsulation has a second antimicrobial minimal inhibitory concentration to at least one of Gram Positive cocci and a Gram Negative rod, wherein the second microbial minimal inhibitory concertation is greater than the first microbial minimal inhibitory concentration.

10. The composition of claim 9, wherein the antimicrobial efficacy of dielectric-silver nanocomposite material for the Gram Negative rod lies between that of a metallic form of silver, and an ionic form of silver.

11. The composition of claim 1, wherein the dielectric-silver nanocomposite material has a less negative Zeta potential relative to that of an isolated silver nanoparticle lacking the dielectric material encapsulation, wherein the Zeta potential of the dielectric-silver nanocomposite material is between −30 mV and −40 mV.

12. A nanocomposite material comprising:
a silver nanoparticle that is co-loaded with an ionic silver, the silver from each of the silver nanoparticle and the ionic silver having a first plasmon resonance, and a dielectric material encapsulating each of the silver nanoparticle and the ionic silver to form a dielectric-silver nanocomposite material;
wherein silver from each of the silver nanoparticle and the ionic silver chelates with a matrix of the dielectric material, such that the silver from each of the silver nanoparticle and the ionic silver has a second plasmon resonance upon chelation; and
wherein the second plasmon resonance is less than the first plasmon resonance such that the dielectric-silver nanocomposite material is colorless.

13. The nanocomposite material of claim 12, wherein the dielectric material surrounding each of the silver nanoparticle and the ionic silver renders the dielectric-silver nanocomposite material transparent.

14. The nanocomposite material of claim 12, wherein the silver nanoparticle is a silver nanoparticle of a plurality of silver nanoparticles, and a capping agent adsorbs a surface of each of the plurality of silver nanoparticles, wherein the capping agent controls nucleation of each of the plurality of silver nanoparticles within the matrix of the dielectric material to inhibit aggregation thereof.

15. The nanocomposite material of claim 12, wherein the silver nanoparticle is a sustained-release silver nanoparticle, and the ionic silver is a sustained-release silver ion, wherein a sustained-release of each of the silver-nanoparticle and the ionic silver promotes antimicrobial characteristics, without affecting transparency of the dielectric-silver nanocomposite material.

16. A method for preparing the nanocomposite material of claim 12, the method comprising: forming from a silver-precursor mixture comprising a silver nanoparticle and an ionic silver; and mixing the mixture with a dielectric-material precursor to form a dielectric-silver nanocomposite material, the dielectric-silver nanocomposite material comprising the silver nanoparticle that is co-loaded with the ionic silver, wherein silver from each of the silver nanoparticle and the ionic silver chelates with a matrix of a dielectric material, and a surface plasmon band absorption of the dielectric-silver nanocomposite material lies outside a range of a visible region.

17. The method of claim 16, wherein the dielectric material surrounding each of the capping-agent-coated silver nanoparticle and the ionic silver renders the dielectric-silver nanocomposite material transparent.

18. The method of claim 16, wherein the capping-agent-coated silver nanoparticle is a capping-agent-coated silver nanoparticle of a plurality of capping-agent-coated silver nanoparticles, and a capping agent adsorbs a surface of each of the plurality of capping-agent-coated silver nanoparticles, wherein the capping agent controls nucleation of each of the plurality of capping-agent-coated silver nanoparticles within a matrix of the dielectric material to inhibit aggregation thereof.

19. The method of claim 16, wherein a sustained-release of each of the capping-agent-coated silver-nanoparticle and the ionic silver promotes antimicrobial characteristics, without affecting transparency of the dielectric-silver nanocomposite material.

20. The method of claim 16, wherein the dielectric-silver nanocomposite material has enhanced Zeta potential relative to that of an isolated silver nanoparticle lacking the dielectric material encapsulation, wherein the Zeta potential of the dielectric-silver nanocomposite material is between 30 mV and 40 mV.

21. A treatment method comprising applying a composition in accordance with claim 1 to a substrate for antibacterial purposes.

* * * * *